(12) United States Patent
Suga et al.

(10) Patent No.: US 8,188,260 B2
(45) Date of Patent: May 29, 2012

(54) VERSATILE ACYLATION CATALYTIC RNAS AND USES THEREOF

(75) Inventors: Hiroaki Suga, Tokyo (JP); Hiroshi Murakami, Tokyo (JP)

(73) Assignee: The University of Tokyo, Tokyo (JP)

( * ) Notice: Subject to any disclaimer, the term of this patent is extended or adjusted under 35 U.S.C. 154(b) by 399 days.

(21) Appl. No.: 12/086,125

(22) PCT Filed: Dec. 5, 2006

(86) PCT No.: PCT/JP2006/324196
§ 371 (c)(1),
(2), (4) Date: May 21, 2009

(87) PCT Pub. No.: WO2007/066627
PCT Pub. Date: Jun. 14, 2007

(65) Prior Publication Data
US 2009/0281280 A1 Nov. 12, 2009

(30) Foreign Application Priority Data
Dec. 6, 2005 (JP) ................................ 2005-352243

(51) Int. Cl.
C07H 21/04 (2006.01)
C07H 21/02 (2006.01)
C12N 15/85 (2006.01)

(52) U.S. Cl. ... 536/24.5; 435/325; 536/23.1; 536/24.31; 536/24.33

(58) Field of Classification Search .................. None
See application file for complete search history.

(56) References Cited

U.S. PATENT DOCUMENTS

| | | | |
|---|---|---|---|
| 5,475,096 A | 12/1995 | Gold et al. | |
| 5,990,142 A | 11/1999 | Carganico et al. | |
| 6,063,566 A | 5/2000 | Joyce | |
| 7,001,723 B1 | 2/2006 | Suga et al. | |
| 2003/0228593 A1 | 12/2003 | Suga et al. | |

FOREIGN PATENT DOCUMENTS

| | | |
|---|---|---|
| WO | WO 99/36517 A2 | 7/1999 |
| WO | WO 03/070740 A1 | 8/2003 |

OTHER PUBLICATIONS

Brenner et al., Proc. Natl. Acad. Sci. USA, vol. 89, pp. 5381-5383, Jun. 1992.
Bain et al., J. Am. Chem. Soc, 111, pp. 8013-8014, May 22, 1989.
Hohsaka et al., J. Am. Chem. Soc., 118, pp. 9778-9779, Apr. 30, 1996.
Hirao et al., Nature Biotechnology., vol. 20, pp. 177-182, Feb. 2002.
Murakami., J. Am. Chem. Soc., vol. 124, No. 24, pp. 6834-6835, Feb. 8, 2002.
Suga et al., J. Am. Chem. Soc., vol. 120, No. 6, pp. 1151-1156, 1998.
Bessho et al., "A tRNA aminoacylation system for non-natural amino acids based on a programmable ribozyme," Nature Biotechnology, Vo. 20, No. 7, Jul. 1, 2002, pp. 723-728, XP-002374062.
Extended European Search Report dated Sep. 20, 2010 for corresponding European Application No. 06833951.4.
Hager et al., "Ribozymes: aiming at RNA replication and protein synthesis," Chemistry and Biology, Current Biology, vol. 3, No. 9, pp. 717-725, Sep. 1, 1996, XP-002104957.
Lohse et al., "Ribozyme-catalysed amino-acid transfer reactions," Nature, May 30, 1996, vol. 381, No. 6581, pp. 442-444, XP-002599075.
Murakami et al., "Flexizyme as a versatile tRNA acylation catalyst and the application for translation," Nucleic Acids Symposium Series, 2006, No. 50, pp. 35-36, XP-002599076.
Pan, "Novel and variant ribozymes obtained through in vitro selection,"Current Opinion in Chemical Biology, vol. 1, No. 1, Jun. 1, 1997, pp. 17-25, XP-002109694.
Ramaswamy et al., "Designer Ribozymes: Programming the tRNA Specifically into Flexizyme," Journal of the American Chemical Society, vol. 126, No. 37, Sep. 22, 2004, pp. 11454-11455, XP-002599008.
Murakami H. et al., A versatile tRNA aminoacylation catalyst based on RNA, Chem. Biol., 2003, vol. 10, No. 7, p. 655-62.
Murakami H. et al., Using a solid-phase ribozyme aminoacylation system to reprogram the genetic code, Chem. Biol., 2003, vol. 10, No. 11, p. 1077-84.
Hiroshi Murakami et al., "Jinko Ribozyme no Shinka to Iden Ango Kaihen eno Oyo", 28th Annual Meeting of the Molecular Biology Society of Japan Koen Yoshishu, Nov. 25, 2005, p. 129, YG4H-1.
Murakami H. et al., A Highly flexible tRNA acylation Method for non-natural polypeptide synthesis, Nat. Methods., May 2006, vol. 3, No. 5, p. 357-9.
Hiroshi Murakami et al., "Seimei o Design suru Gosei Seibutsugaku Central Dogma o Tukuri Kaeru", Bionics, Mar. 1, 2006, vol. 3, No. 3, p. 34-9.
Hiroshi Murakami et al., "Flexizyme System: mRNA o Igata to Shita Hitennen Peptide no Gosei eno Oyo", CSJ: The Chemical Society of Japan Koen Yokoshu, Mar. 13, 2006, vol. 86th, No. 2, p. 895, 3 G4-43.

*Primary Examiner* — Amy Bowman
(74) *Attorney, Agent, or Firm* — Birch, Stewart, Kolasch & Birch, LLP

(57) ABSTRACT

An object of the present invention is to provide novel ribozyme systems capable of catalyzing tRNA acetylation using various carboxylic acids as acyl donors and uses thereof. Disclosed is a ribozyme catalyzing tRNA acetylation having a structure consisting of the RNA sequence represented by: (formula 1) $P1-Z_1Z_2Z_3Z_4(N^1)_1(N^1)_2 \ldots (N^1)_p-P2-(N^2)_1(N^2)_2 \ldots (N^2)_q Y_1Y_2Y_3-(N^3)_1(N^3)_2-N^4GGN$ wherein $(N^1)_1-(N^1)_p$ each independently represent any monoribonucleotide of U, C, A, and G; p represents 3 or 4; $(N^2)_1-(N^2)_q$ each independently represent any monoribonucleotide of U, C, A, and G; q represents 5 or 6; $(N^3)_1-(N^3)_2$ each independently represent any monoribonucleotide of U, C, A, and G; $N^4$ represents any monoribonucleotide of U, C, A, and G; $Z_1-Z_4$ each independently represent C or G; $Y_1-Y_3$ each independently represent C or G; N represents a monoribonucleotide complementary to A or G; and P1 and P2 represent a domain consisting of any RNA sequence capable of having a stem-loop structure.

18 Claims, 10 Drawing Sheets

Solid lines indicate hydrogen bonds in the three-dimensional structure of the tRNA.

Modified nucleosides are shown in circles.

D: Dihydrouridine

Ψ: Pseudouridine

Y: Modified purine residue m: Methyl group (a) Cloverleaf structure of yeast phenylalanine tRNA N(1) consists of 3 or 4 ribonucleotides.
N(2) consists of 5 or 6 ribonucleotides.
N(3) consists of 2 ribonucleotides.
N(4) consists of one ribonucleotide.
P1 and P2 represent a step loop.

pink : recognition site (aromatic ring)
blue : leaving group
red : reaction site

Figure 7 a
```
        A A
       G   A
       C—G
       C—G 30
       C—G
    20 C—G A
      U   U
      A   C
A A10           C
 A GAUUCCG     A
  | | | | |    U
 A  CUAGG 5'   G
  G            G
               C
               GUUAGGU 3'
               40
```
Superflexizyme 2 b
```
        A A
       G   A
       C—G
       C—G 30
       C—G
    20 G—G A
      G   U
      C   U
A A10           A
 A GAUUCCG     G
  | | | | |    C
 A  CUAGG 5'   GUUAGGU 3'
  G            40
```
Superflexizyme 1

Figure 8

| ribozyme | Flexizyme | | | Superflexizyme 2 | | | Flexizyme | | | Superflexizyme 2 | | |
|---|---|---|---|---|---|---|---|---|---|---|---|---|
| esters | CME | | DBE | CME | | DBE | CME | | DBE | CME | | DBE |
| | Phe | Leu | Leu | Phe | Leu | Leu | Phe | Leu | Leu | Phe | Leu | Leu |
| lanes | 1 | 2 | 3 | 4 | 5 | 6 | 7 | 8 | 9 | 10 | 11 | 12 | tRNA-3' (Ox)

(I) ➡ —         —         —

(II) ➡ — — — — — — — — — — — —

(III) ⇨ ■ ■ ■ ■ ■ ■ ■ ■ ■ ■ ■ ■

Yields (%)  30  2   2   12  1   30

|  | Flexizyme | Super-flexizyme 1 | | Super-flexizyme 1 | | | Super-flexizyme 2 | | |
|---|---|---|---|---|---|---|---|---|---|
| ester | CME | | | DBE | DBE | CBT | DBE | DBE | CBT |
| a.a. | Phe Phe | Phe | Phe | Leu | Val | Val | Leu | Val | Val |
| Time (h) | 0.16 1 | 0.16 | 1 | 2 | 6 | 6 | 2 | 6 | 6 |
| lanes | 1 2 | 3 | 4 | 5 | 6 | 7 | 8 | 9 | 10 |

(I)

(II)

(III)

Yields (%)  11  31  26  40  17  1  11  29  5  0

US 8,188,260 B2

SEQUENCE LISTING

<160> NUMBER OF SEQ ID NOS: 25

<210> SEQ ID NO 1
<211> LENGTH: 7
<212> TYPE: RNA
<213> ORGANISM: Artificial Sequence
<220> FEATURE:
<223> OTHER INFORMATION: synthetic oligonucleotide

<400> SEQUENCE: 1 ccgcggc                                                                    7

<210> SEQ ID NO 2
<211> LENGTH: 14
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (14)..(14)
<223> OTHER INFORMATION: random nuclotide
<220> FEATURE:
<221> NAME/KEY: misc_feature
<222> LOCATION: (14)..(14)
<223> OTHER INFORMATION: random nucleotide

<400> SEQUENCE: 2
gauuagcguu aggn                                                           14

<210> SEQ ID NO 3
<211> LENGTH: 7
<212> TYPE: RNA
<213> ORGANISM: Artificial Sequence
<220> FEATURE:
<223> OTHER INFORMATION: synthetic oligonucleotide

<400> SEQUENCE: 3 ccgcauc                                                                    7

<210> SEQ ID NO 4
<211> LENGTH: 15
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (15)..(15)
<223> OTHER INFORMATION: random nucleotide

<400> SEQUENCE: 4
uacauggcgu uaggn                                                          15

<210> SEQ ID NO 5
<211> LENGTH: 14
<212> TYPE: RNA
<213> ORGANISM: Artificial Sequence
<220> FEATURE:
<223> OTHER INFORMATION: synthetic oligonuclotide
<220> FEATURE:
<221> NAME/KEY: stem_loop
<222> LOCATION: (1)..(14)

<400> SEQUENCE: 5
ggaucgaaag auuu                                                           14

```
<210> SEQ ID NO 6
<211> LENGTH: 10
<212> TYPE: RNA
<213> ORGANISM: Artificial Sequence
<220> FEATURE:
<223> OTHER INFORMATION: synthetic oligonucleotide
<220> FEATURE:
<221> NAME/KEY: stem_loop
<222> LOCATION: (1)..(10)

<400> SEQUENCE: 6
cccgaaaggg                                                                10

<210> SEQ ID NO 7
<211> LENGTH: 45
<212> TYPE: RNA
<213> ORGANISM: Artificial Sequence
<220> FEATURE:
<223> OTHER INFORMATION: catalytic RNA "super Fx 1"

<400> SEQUENCE: 7
ggaucgaaag auuccgcgg ccccgaaagg ggauuagcgu uaggu              45

<210> SEQ ID NO 8
<211> LENGTH: 46
<212> TYPE: RNA
<213> ORGANISM: Artificial Sequence
<220> FEATURE:
<223> OTHER INFORMATION: catalytic RNA "super Fx 2"

<400> SEQUENCE: 8
ggaucgaaag auuccgcau ccccgaaagg guacauggcg uuaggu             46

<210> SEQ ID NO 9
<211> LENGTH: 46
<212> TYPE: RNA
<213> ORGANISM: Artificial Sequence
<220> FEATURE:
<223> OTHER INFORMATION: catalytic RNA "1-N"
<220> FEATURE:
<221> NAME/KEY: misc_feature
<222> LOCATION: (46)..(46)
<223> OTHER INFORMATION: random nucleotide

<400> SEQUENCE: 9
ggaucgaaag auuccgcgg ccccgaaagg ggauuagcgu uaggun             46

<210> SEQ ID NO 10
<211> LENGTH: 47
<212> TYPE: RNA
<213> ORGANISM: Artificial Sequence
<220> FEATURE:
<223> OTHER INFORMATION: catalytic RNA "2-N"
<220> FEATURE:
<221> NAME/KEY: misc_feature
<222> LOCATION: (47)..(47)
<223> OTHER INFORMATION: random nucleotide

<400> SEQUENCE: 10
ggaucgaaag auuccgcau ccccgaaagg guacauggcg uuaggun            47

<210> SEQ ID NO 11
<211> LENGTH: 46
<212> TYPE: RNA
<213> ORGANISM: Artificial Sequence
<220> FEATURE:
<223> OTHER INFORMATION: catalytic RNA "1-A"

<400> SEQUENCE: 11
```

```
ggaucgaaag auuccgcgg ccccgaaagg ggauuagcgu uaggua          46
```

<210> SEQ ID NO 12
<211> LENGTH: 47
<212> TYPE: RNA
<213> ORGANISM: Artificial Sequence
<220> FEATURE:
<223> OTHER INFORMATION: catalytic RNA "2-A"

<400> SEQUENCE: 12

```
ggaucgaaag auuccgcau ccccgaaagg guacauggcg uuaggua         47
```

<210> SEQ ID NO 13
<211> LENGTH: 45
<212> TYPE: DNA
<213> ORGANISM: Artificial Sequence
<220> FEATURE:
<223> OTHER INFORMATION: synthetic oligonucleotide "eFxR45"
      complementary to the super Fx 1

<400> SEQUENCE: 13

```
acctaacgct aatccccttt cggggccgcg gaaatctttc gatcc          45
```

<210> SEQ ID NO 14
<211> LENGTH: 36
<212> TYPE: DNA
<213> ORGANISM: Artificial Sequence
<220> FEATURE:
<223> OTHER INFORMATION: "P3" primer

<400> SEQUENCE: 14

```
gtaatacgac tcactatagg atcgaaagat ttccgc                    36
```

<210> SEQ ID NO 15
<211> LENGTH: 25
<212> TYPE: DNA
<213> ORGANISM: Artificial Sequence
<220> FEATURE:
<223> OTHER INFORMATION: "P4" primer

<400> SEQUENCE: 15

```
gcatatgtaa tacgactcac tatag                                25
```

<210> SEQ ID NO 16
<211> LENGTH: 19
<212> TYPE: DNA
<213> ORGANISM: Artificial Sequence
<220> FEATURE:
<223> OTHER INFORMATION: "eFxR19" primer

<400> SEQUENCE: 16

```
tacctaacgc taatcccct                                       19
```

<210> SEQ ID NO 17
<211> LENGTH: 46
<212> TYPE: DNA
<213> ORGANISM: Artificial Sequence
<220> FEATURE:
<223> OTHER INFORMATION: synthetic oligonucleotide "dnFxR46"
      complementary to the super Fx 2

<400> SEQUENCE: 17

```
acctaacgcc atgtacccctt tcggggatgc ggaaatcttt cgatcc        46
```

<210> SEQ ID NO 18
<211> LENGTH: 19
<212> TYPE: DNA

```
<213> ORGANISM: Artificial Sequence
<220> FEATURE:
<223> OTHER INFORMATION: "dnFxR19" primer

<400> SEQUENCE: 18
acctaacgcc atgtaccct                                                    19

<210> SEQ ID NO 19
<211> LENGTH: 76
<212> TYPE: DNA
<213> ORGANISM: Artificial Sequence
<220> FEATURE:
<223> OTHER INFORMATION: synthetic oligonucleotide "tRNAasncua76"
      complementary to the tRN Aasncua

<400> SEQUENCE: 19
tggtgcctct gactggactc gaaccagtga catacggatt tagagtccgc cgttctaccg      60
actgaactac agaggc                                                      76

<210> SEQ ID NO 20
<211> LENGTH: 46
<212> TYPE: DNA
<213> ORGANISM: Artificial Sequence
<220> FEATURE:
<223> OTHER INFORMATION: "tRNAasncua46" primer

<400> SEQUENCE: 20
acgcatatgt aatacgactc actatagcct ctgtagttca gtcggt                     46

<210> SEQ ID NO 21
<211> LENGTH: 20
<212> TYPE: DNA
<213> ORGANISM: Artificial Sequence
<220> FEATURE:
<223> OTHER INFORMATION: "tRNAasncua20" primer

<400> SEQUENCE: 21
tggtgcctct gactggactc                                                  20

<210> SEQ ID NO 22
<211> LENGTH: 45
<212> TYPE: RNA
<213> ORGANISM: Artificial Sequence
<220> FEATURE:
<223> OTHER INFORMATION: catalytic RNA "Flexizyme"

<400> SEQUENCE: 22
ggaucgaaag auuuccgcag gcccgaaagg guauuggcgu uaggu                      45

<210> SEQ ID NO 23
<211> LENGTH: 65
<212> TYPE: RNA
<213> ORGANISM: Artificial Sequence
<220> FEATURE:
<223> OTHER INFORMATION: catalytic RNA "Flexiresin"

<400> SEQUENCE: 23
ggaucgaaag auuuccgcag gcccgaaagg guauuggcgu uagguaaaaa aaaaaaaaa       60 aaaaa                                                                  65

<210> SEQ ID NO 24
<211> LENGTH: 14
<212> TYPE: RNA
<213> ORGANISM: Artificial Sequence
<220> FEATURE:
<223> OTHER INFORMATION: Synthetic
```

```
<400> SEQUENCE: 24
ggaucgaaag aucc                                                                  14

<210> SEQ ID NO 25
<211> LENGTH: 10
<212> TYPE: RNA
<213> ORGANISM: Artificial Sequence
<220> FEATURE:
<223> OTHER INFORMATION: Synthetic

<400> SEQUENCE: 25
cccuucgggg                                                                       10
```

VERSATILE ACYLATION CATALYTIC RNAS AND USES THEREOF

TECHNICAL FIELD

The present invention relates to ribozymes as novel artificial catalysts that catalyze tRNA acylation and uses thereof.

BACKGROUND ART

Aminoacyl-tRNA Synthetases (ARSs)

Genetic information contained in DNA is translated into an amino acid sequence on the basis of the genetic code table. During translation, in existing natural cells, a transfer RNA (tRNA) is used as an adapter for correctly combining an amino acid with a codon. The tRNA as an adapter recognizes an amino acid on one side and a codon on the other side. Natural tRNAs are small RNAs of about 80 nucleotides in length.

An amino acid first binds the 3' end of a tRNA, and then it is transported to the ribosome where protein synthesis occurs. In the ribosome, an anticodon of the tRNA having transported the amino acid pairs with a three-base codon of a messenger RNA (mRNA) into which genetic information has been transcribed, whereby the codon matches the specific tRNA and it is further translated into one of the twenty amino acids defined in the genetic code table.

The reaction in which a specific amino acid is attached to its cognate tRNA is called tRNA aminoacylation. The tRNA aminoacylation is catalyzed by an aminoacyl-tRNA synthetase (ARS). Twenty ARSs are provided for the respective twenty natural amino acids. Using a specific ARS, each amino acid is attached, through an ester bond at the carboxyl terminus, to 3'- or 2'-OH of the sugar (ribose) of the 3'-terminal adenosine residue of a specific tRNA molecule to which the amino acid can bind.

The mechanism by which an ARS selectively recognizes its substrate amino acid and tRNA is very delicate and complex. In most cells, ARSs vary from one amino acid to another, and the correct amino acid has the highest affinity for the active site cavity of an ARS. Due to such strict substrate specificity, ARSs cannot accept nonnatural amino acids as substrates in nature. Structural and chemical complementarity between ARSs and tRNAs extends over a wide range including anticodon, amino acid acceptor stem and ribose-phosphate skeleton, and ARSs sense various characteristics of tRNAs and strictly discriminate their cognate tRNAs from other tRNA molecular species.

Artificial Ribozymes

A ribozyme refers to an RNA having an enzyme activity (catalytic ability), i.e., an RNA catalyst. The term ribozyme is a fusion of two words, ribonucleic acid (RNA) and enzyme.

Typical known examples in nature include ribosomes responsible for protein synthesis, and ribozymes that catalyze the cleavage of RNAs such as RNaseP, hammerhead ribozymes, etc. These are important "fossilized" presences supporting the "RNA world hypothesis" proposing that RNA functioned as a catalyst at an early stage of life. The RNA world hypothesis is based on the premise that all biochemical reactions can be catalyzed by RNA, but only two types of catalytic activities as described above have been found in nature. Thus, RNA catalysts having various catalytic activities were artificially created by in vitro evolution in order to verify the credibility of this hypothesis.

In vitro molecular evolution is an approach for newly evolving a nucleic acid molecule having an intended activity from a randomly artificially synthesized nucleic acid library. This approach was originated by Brennen et al., who reported a method involving constructing a gene pool and selecting a molecule catalyzing a desired reaction in vitro and isolating it in order to identify a novel catalyst (non-patent document 1). According to a modification of this method known as SELEX method (Systematic Evolution of Ligands by EXponential enrichment), nucleic acid molecules specifically interacting a target molecule can be identified (patent documents 1-3). By repeating the step of selecting active molecules from a gene pool consisting of oligonucleotides having as many as $10^{15}$ different random nucleotide sequences (having known primer-binding sites at both ends) and the step of amplifying them by PCR or other techniques, the initially very low proportion of molecules having a desired activity in the entire pool is exponentially increased and finally active molecules can be isolated. This method is used to isolate a ligand or aptamer having a binding activity toward a target molecule such as a protein, and the concept of this method was further expanded to develop a method for in vitro molecular evolution of a ribozyme. In this case, active RNAs acting as self-modified (cis or intramolecular) catalysts are selected from an RNA pool containing random nucleotide sequences, and amplified in the same manner as described above. Novel ribozymes having phosphodiestarase or amidase activity were identified by this method (patent document 3).

ARS Ribozymes

In nature, ARSs are proteins, and no ARS ribozyme has been discovered. Thus, attempts were made to create not naturally occurring ARS ribozymes (ribozymes functioning as aminoacyl-tRNA synthetases) using in vitro molecular evolution (patent documents 2, 4, 5, non-patent documents 2, 3).

Using an ARS ribozyme that was previously created by us, an aminoacyl-tRNA can be synthesized only by mixing a modestly activated amino acid and tRNA with the catalyst ribozyme (which can be immobilized to a column). The ARS ribozyme created by us was designed to recognize the terminal consensus sequence (RCCA-3' wherein R is the discriminator base A or G at position 73) of tRNAs so that it can accept all tRNAs as substrates and it can also accept any amino acid substrate having an aromatic ring in the side chain such as natural aromatic amino acids (phenylalanine, tyrosine, tryptophan) and various phenylalanine analogs having various substituents at the para-position of the phenylalanine side chain among nonnatural amino acids. We named this ARS ribozyme as Flexizyme after its flexibility with phenylalanine analogs and tRNAs.

Referring to FIG. 1, the structure of Flexizyme is explained. Flexizyme consists of 45 nucleotides (SEQ ID NO: 22), and contains a GGU motif and a U-rich domain. The GGU motif (G43-U45) is complementary to A73-C75 (wherein A is the discriminator base at position 73) of ACCA-3' at the 3' end (amino acid acceptor end) of tRNA and considered to correspond to the tRNA recognition site. On the other hand, the single-stranded U-rich domain (U32-U35) is considered to be responsible for the recognition of amino acids. In addition, a GGCG sequence (G36-G39) is thought to be important for the catalytic activity of the ribozyme (non-patent document 3).

Unnatural Amino Acid Mutagenesis

Proteins are polymers made of the 20 natural amino acids and perform many functions by various combinations of these amino acids. Amino acid changes are often made during studies of protein functions, but mutations by conventional mutagenesis are limited only within the framework of the twenty natural amino acid. Unnatural amino acid mutagenesis is a method developed to remove this framework and to incorporate various amino acids other than natural amino acids (non-patent documents 4, 5).

Site-specific incorporation of nonnatural amino acids started from the studies of both groups of Schultz and Chamberlin in 1898 (non-patent documents 4, 5). They used an amber codon (UAG) among stop codons to encode a nonnatural amino acid to site-specifically incorporate it into a protein. This method comprises the following three steps. First, a mutant gene having an amber codon (TAG) substituted for the codon at the position to which a nonnatural amino acid is to be incorporated is prepared. Then, a suppressor tRNA aminoacylated with the nonnatural amino acid is prepared. The mutant gene and the suppressor tRNA are added to a cell-free translation system. Thus, the tRNA aminoacylated with the nonnatural amino acid suppresses the cognate amber codon, whereby the nonnatural amino acid is site-specifically incorporated into the position of the amber codon.

If two or more nonnatural amino acids are to be incorporated, other codons encoding the nonnatural amino acids are needed in addition to the amber codon. However, the other two stop codons cannot be used as codons encoding nonnatural amino acids in a cell-free translation system. (The ochre codon has a low suppression efficiency, and the opal codon is often read through.) The other codons in the codon table are assigned to natural amino acids. Thus, Shishido's group expanded codons to four bases and developed a method for encoding nonnatural amino acids by four-base codons by (non-patent document 6, etc.). Normally, ribosomes add one amino acid by recognizing three bases as one codon. If a tRNA having a four-base anticodon is used, however, a programmed frameshift occurs on the cognate four-base codon so that the four-base codon can encode a nonnatural amino acid. In principle, this method allows expansion to the 23rd and 24th amino acids and further nonnatural amino acids. Another method for codon expansion using unnatural bases was also developed (non-patent document 7).

Techniques for incorporating nonnatural amino acids into proteins are used by only limited researchers despite their usefulness. The prime reason for this is difficulty in the synthesis of tRNAs aminoacylated with nonnatural amino acids. As described above, natural ARSs cannot accept nonnatural amino acids or unrelated tRNAs because of the strict substrate recognition. Thus, very laborious chemical methods (chemical aminoacylation) have been used to aminoacylate tRNAs with nonnatural amino acids. Methods using altered ARS protein enzymes designed to accept nonnatural amino acids as substrates have also been developed. However, unnatural amino acid mutagenesis in cells using an ARS protein enzyme altered from an existing protein enzyme requires the altered ARS protein enzyme to have high substrate specificity for the nonnatural amino acid, but it is impractical to prepare altered ARS protein enzymes for all of an enormous number of nonnatural amino acids reported so far, and only one approach currently applicable to all amino acids is expensive and complicated chemical aminoacylation. On the other hand, we previously developed a method using an ARS ribozyme capable of attaching nonnatural amino acids (phenylalanine analogs) to tRNAs (patent documents 4, 5, non-patent documents 2, 3 prepared by us).

Chemical aminoacylation requires very complex and expensive synthetic procedures that can be performed in only a few laboratories in the world. A protein ARS altered from a natural enzyme must be freshly prepared to suit each type of amino acid used. Moreover, methods using altered protein ARS enzymes require a combination of a suppressor tRNA that is not aminoacylated by protein enzymes present in an in vitro protein synthesis system and a protein enzyme aminoacylating it. Such a combination must be screened from other species, but it is impractical to screen it for the twenty amino acids because protein enzymes normally also often show strict recognition for tRNAs.

An ARS capable of aminoacylating any tRNA with any amino acid would allow site-directed unnatural amino acid mutagenesis at will, but such an ARS has not been reported.

REFERENCES

Patent document 1: U.S. Pat. No. 5,475,096.
Patent document 2: U.S. Pat. No. 5,990,142.
Patent document 3: U.S. Pat. No. 6,063,566.
Patent document 4: JPA 2003-514572.
Patent document 5: WO 03/070740 A1.
Non-patent document 1: Brennen et al., (1992) Proc. Natl. Acad. Sci., USA, 89, 5381-5383.
Non-patent document 2: H. Murakami, H. Saito, and H. Suga, (2003), Chemistry & Biology, Vol. 10, 655-662.
Non-patent document 3: H. Murakami, D. Kourouklis, and H. Suga, (2003), Chemistry & Biology, Vol. 10, 1077-1084.
Non-patent document 4: Bain, J. D. et al, (1989), J. Am. Chem. Soc., 111, 8013-8014.
Non-patent document 5: Noren, C. J. et al, (1989), Science, 244, 182-188.
Non-patent document 6: Hosaka, T. et al., (1996) Am. Chem. Soc., 118, 9778-9779.
Non-patent document 7: Hirao, I. et al., (2002) Nat. Biotechnol., 20, 177-182.

DISCLOSURE OF THE INVENTION

Problems to be Solved by the Invention

An object of the present invention is to provide novel ribozyme systems capable of catalyzing the reaction of attaching various amino acids, lactic acid and other carboxylic acids to tRNAs, i.e. catalyzing tRNA acylation using various carboxylic acids as donors for acyl groups and uses thereof.

Means for Solving the Problems

Accordingly, the present invention provides the following.
(1) A ribozyme catalyzing tRNA acylation having a structure consisting of an RNA sequence represented by the general formula below:

$$P1-Z_1Z_2Z_3Z_4(N^1)_1(N^1)_2\ldots(N^1)_p\text{-}P2\text{-}(N^2)_1(N^2)_2\ldots(N^2)_q Y_1Y_2Y_3(N^3)_1(N_3)_2N^4 G G \underline{N}$$

wherein P1 and P2 represent a domain consisting of any RNA sequence capable of having a stem-loop structure; $(N^1)_1$-$(N^1)_p$ each independently represent any monoribonucleotide of U, C, A and G; p represents 3 or 4; $(N^2)_1$-$(N^2)_q$ each independently represent any monoribonucleotide of U, C, A and G;
q represents 5 or 6; $(N^3)_1$-$(N^3)_2$ each independently represent any monoribonucleotide of U, C, A and G; $N^4$ represents any monoribonucleotide of U, C, A and G; $Z_1$-$Z_4$ each independently represent C or G; $Y_1$-$Y_3$ each independently represent C or G;
$\underline{N}$ represents a monoribonucleotide complementary to A or G;
$\underline{U}$ represents an uracil nucleotide; C represents a cytosine nucleotide; A represents an adenine nucleotide; and
G represents a guanine nucleotide;

wherein the ribozyme recognizes a tRNA to bind it via the 3'-terminal GGN motif and said GGN motif is complementary to a nucleotide sequence at positions 75-73 at the 3' end of the tRNA binding the ribozyme.

(2) A ribozyme catalyzing tRNA acylation having a structure consisting of an RNA sequence represented by the general formula below:

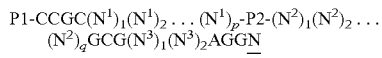
P1-CCGC$(N^1)_1(N^1)_2 \ldots (N^1)_p$-P2-$(N^2)_1(N^2)_2 \ldots (N^2)_q$GCG$(N^3)_1(N^3)_2$AGG$\underline{N}$ wherein P1 and P2 represent a domain consisting of any RNA sequence capable of having a stem-loop structure; $(N^1)_1$-$(N^1)_p$ each independently represent any monoribonucleotide of U, C, A and G; p represents 3 or 4; $(N^2)_1$-$(N^2)_q$ each independently represent any monoribonucleotide of U, C, A and G;
q represents 5 or 6; $(N^3)_1$-$(N^3)_2$ each independently represent any monoribonucleotide of U, C, A and G; U represents an uracil nucleotide; C represents a cytosine nucleotide;
A represents an adenine nucleotide; G represents a guanine nucleotide; and N represents a monoribonucleotide complementary to A or $\overline{G}$;
wherein the ribozyme recognizes a tRNA to bind it via the 3'-terminal GGN motif and said GGN motif is complementary to a nucleotide sequence at positions 75-73 at the 3' end of the tRNA binding the ribozyme.

(3) A ribozyme catalyzing tRNA acylation having a structure consisting of an RNA sequence represented by formula (I) or (II) below:

(SEQ ID NOS: 1 and 2)
P1-CCGCGGC-P2-GAUUAGCGUUAGG$\underline{N}$ (I)

(SEQ ID NOS: 3 and 4)
P1-CCGCAUC-P2-UACAUGGCGUUAGG$\underline{N}$ (II)

wherein P1 and P2 represent a domain consisting of any RNA sequence capable of having a stem-loop structure; U represents a uracil nucleotide; C represents a cytosine nucleotide; A represents an adenine nucleotide; G represents a guanine nucleotide; and N represents a monoribonucleotide complementary to A or $\overline{G}$;
wherein the ribozyme recognizes a tRNA to bind it via the 3'-terminal GGN motif and said GGN motif is complementary to a nucleotide sequence at positions 75-73 at the 3' end of the tRNA binding the ribozyme.

(4) The ribozyme of (1) to (3) above wherein P1 and P2 each independently consist of an RNA sequence represented by the formula below:

wherein B represents any single-stranded loop consisting of 1-8 ribonucleotides selected from U, C, A or G; $Q_1$-$Q_n$ each independently represent any monoribonucleotide of U, C, A and G; $R_1$-$R_n$ represent any monoribonucleotide of U, C, A and G selected in such a manner that they can preferentially assume a double-stranded structure by forming wholly or partially complementary base pairs with $Q_1$-$Q_n$; and n represents an integer of 1-10.

(5) The ribozyme of (4) wherein the single-stranded loop represented by B is a stable tetraloop.

(6) The ribozyme of (1) to (5) above wherein P1 and P2 consist of RNA sequences represented by:

P1: GGAUCGAAAGAUUU; (SEQ ID NO: 5)

P2: CCCGAAAGGG. (SEQ ID NO: 6)

(7) A ribozyme catalyzing tRNA acylation consisting of any one of RNA sequences (a)-(d) below:

(a) (SEQ ID NO: 7)
GGAUCGAAAGAUUUCCGCGGCCCCGAAAGGGGAUUAGCGUUAGGU;

(b) (SEQ ID NO: 8)
GGAUCGAAAGAUUUCCGCAUCCCCGAAAGGGUACAUGGCGUUAGGU;

(c) an RNA sequence identical to sequence (a) except that U at the 3' end has been replaced by any nucleotide designed to be complementary to nucleotide 73 in the tRNA to be acylated; and (d) an RNA sequence identical to sequence (b) except that U at the 3' end has been replaced by any nucleotide designed to be complementary to nucleotide 73 in the tRNA to be acylated.

(8) The ribozyme of (1) to (7) above, which catalyzes tRNA acylation with a natural amino acid, a nonnatural amino acid, or lactic acid.

(9) A ribozyme catalyzing tRNA acylation, comprising:
(a) a tRNA-binding site recognizing a tRNA to bind it;
(b) an acyl donor substrate-binding site recognizing an acyl donor substrate having a modestly activated ester bond in the acyl leaving group moiety and having an aromatic ring in the side chain or the acyl leaving group to bind it; and
(c) a catalytic activity site having an activity of catalyzing an acyl transfer reaction from the acyl donor substrate to the 3' end of the tRNA;
wherein the tRNA-binding site consists of the 3'-terminal GGU motif of the ribozyme and said GGU motif is complementary to a nucleotide sequence at positions 75-73 of the acyl acceptor stem portion at the 3' end of the tRNA binding the ribozyme, whereby the ribozyme binds the acyl acceptor stem portion via base pairing, thus rapidly inducing an acyl transfer reaction from the acyl donor substrate bound to the acyl donor substrate-binding site to the 3' end of the tRNA, and wherein the nucleotide U on the ribozyme forming a base pair with nucleotide 73 of the tRNA is complementary to A or G and can be mutated to be complementary to it depending on the type of the tRNA, whereby the ribozyme can acylate any tRNA.

(10) The ribozyme of (9) above wherein the acyl donor substrate having an aromatic ring in the acyl leaving group has a structure represented by the formula below:

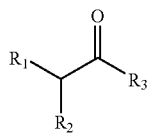

A: Aromatic $R_1$: Any group $R_2$: Any group $R_3$: 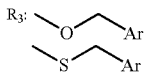

wherein R1 represents a nucleophilic functional group; R2 represents a chemical structure corresponding to a side chain functional group; and R3 represents a leaving group, which is a benzyl ester or thiobenzyl ester containing an aryl group (Ar) having an electron-withdrawing functional group; characterized in that the acyl donor substrate-binding site of the ribozyme recognizes the acyl leaving group R3 of the substrate, whereby the ribozyme can acylate the tRNA with a carboxylic acid having any side chain as the acyl donor substrate.

(11) The ribozyme of (9) or (10) above wherein the acyl donor substrate having an aromatic ring in the acyl leaving group is selected from esterified derivatives of amino acids having an aromatic ring in the acyl leaving group, thioesterified derivatives of amino acids having an aromatic ring in the acyl leaving group, and esterified derivatives of lactic acid having an aromatic ring in the acyl leaving group.

(12) A polynucleotide comprising any one of (a)-(d) below in the molecule:
(a) an RNA constituting a ribozyme of the present invention as defined in any one of (1) to (11) above;
(b) an RNA consisting of a sequence complementary to the RNA of (a) above;
(c) a DNA consisting of a sequence identical to the RNA of (a) above, but U is replaced by T; and
(d) a DNA consisting of a sequence identical to the RNA of (b) above, but U is replaced by T.

(13) A process for preparing an acylated tRNA, comprising steps (a) to (d) below:
(a) providing one or more ribozymes of the present invention;
(b) providing a tRNA;
(c) providing a modestly activated carboxylic acid;
(d) contacting the ribozyme with the tRNA and the modestly activated carboxylic acid to acylate the tRNA; and
(e) isolating the acylated tRNA.

(14) The process of (13) wherein the carboxylic acid is a natural amino acid, nonnatural amino acid, or lactic acid.

(15) The process of (13) wherein the modestly activated carboxylic acid is an esterified derivative of an amino acids, a thioesterified derivative of an amino acid, or an esterified derivative of a carboxylic acid.

(16) The process of (13) wherein the modestly activated carboxylic acid is selected from:
cyanomethyl esters of natural amino acids or nonnatural amino acids having an aromatic ring in the side chain;
3,5-dinitrobenzyl esters of natural amino acids or nonnatural amino acids;
4-chlorobenzyl thioesters of natural amino acids or nonnatural amino acids;
cyanomethyl esters of phenyllacetic acid; and
3,5-dinitrobenzyl esters of phenyllacetic acid or alkyllactic acid.

(17) The process of (13) to (16) above wherein the ribozyme is immobilized to a support.

(18) A ribozyme for use in an immobilized form, consisting of a sequence having one or more adenosine residues added to the 3' end of an RNA constituting the ribozyme of the present invention as defined in (1) to (11) above.

(19) A process for synthesizing an esterified derivative of an amino acid used as a substrate for a ribozyme of the present invention, comprising any one of steps (a) to (c) below:
(a) reacting an amino acid having a Boc-protected amino group with a compound having a halogen at the benzyl position and an electron-withdrawing group in the aromatic group to form an ester, and then removing the Boc protective group with an acid;
(b) condensing an amino acid having a Boc-protected amino group with a compound having a hydroxyl group at the benzyl position and an electron-withdrawing group in the aromatic group using a conventional condensing agent to form an ester, and then removing the Boc protective group with an acid; or
(c) mixing an activated amino acid having a Boc-protected amino group with a compound having a hydroxyl group at the benzyl position and an electron-withdrawing group in the aromatic group to form an ester, and then removing the Boc protective group with an acid;
whereby the leaving group of the esterified derivative of the amino acid serves as the recognition site by the ribozyme.

(20) A process for synthesizing a thioesterified derivative of an amino acid used as a substrate for a ribozyme of the present invention, comprising step (a) or (b) below:
(a) condensing an amino acid having a Boc-protected amino group with a compound having a hydroxyl group at the benzyl position and an electron-withdrawing group in the aromatic group using a conventional condensing agent to form an ester, and then removing the Boc protective group with an acid; or
(b) mixing an activated amino acid having a Boc-protected amino group with a compound having a thiol group at the benzyl position to form an ester, and then removing the Boc protective group with an acid;
whereby the leaving group of the thioesterified derivative of the amino acid serves the recognition site by the ribozyme.

(21) A process for synthesizing an esterified derivative of a carboxylic acid used as a substrate for a ribozyme of the present invention, comprising any one of steps (a) to (c) below:
(a) reacting a carboxylic acid with a compound having a halogen at the benzyl position and an electron-withdrawing group in the aromatic group to form an ester;
(b) condensing a carboxylic acid with a compound having a hydroxyl group at the benzyl position and an electron-withdrawing group in the aromatic group using a conventional condensing agent to form an ester; or
(c) mixing an activated carboxylic acid with a compound having a hydroxyl group at the benzyl position and an electron-withdrawing group in the aromatic group to form an ester;
whereby the leaving group of the esterified derivative of the carboxylic acid serves as a recognition site by the ribozyme.

(22) A process for preparing an acylated tRNA, comprising steps (a) to (e) below:
(a) providing two ribozymes catalyzing tRNA acylation, each consisting of an RNA sequence of (1) or (2) below:

```
                                                (SEQ ID NO: 7)
(1)  GGAUCGAAAGAUUUCCGCGGCCCCGAAAGGGGAUUAGCGUUAGGU (SEQ ID NO: 8)
(2)  GGAUCGAAAGAUUUCCGCAUCCCCGAAAGGGUACAUGGCGUUAGGU
```

(b) providing a tRNA;
(c) providing an esterified derivative or thioesterified derivative of a natural amino acid, nonnatural amino acid or lactic acid;
(d) contacting the ribozymes with the tRNA and the esterified derivative or thioesterified derivative of a natural amino acid, nonnatural amino acid or lactic acid to acylate the tRNA; and
(e) isolating the acylated tRNA.

(23) The process of (22) above wherein the two ribozymes are each immobilized to a support.

(24) A ribozyme for use in an immobilized form, consisting of an RNA comprising a polynucleotide of nucleotide sequence (1-N) or (2-N) below having any oxidatively modifiable nucleotide added to the 3' end of the catalytic RNA molecule to immobilize a ribozyme catalyzing tRNA acylation to a support:

(1-N)                                          (SEQ ID NO: 9)
GGAUCGAAAGAUUUCCGCGGCCCCGAAAGGGGAUUAGCGUUAGGUN where N at the 3' end is any nucleotide added, or (2-N)                                         (SEQ ID NO: 10)
GGAUCGAAAGAUUUCCGCAUCCCCGAAAGGGUACAUGGCGUUAGGUN N at the 3' end is any nucleotide added.
(25) The ribozyme having an adenosine added at the 3' end for use in an immobilized form of (24) above, consisting of an RNA comprising a polynucleotide of nucleotide sequence (1-A) or (2-A) below:

(1-A)                                         (SEQ ID NO: 11)
GGAUCGAAAGAUUUCCGCGGCCCCGAAAGGGGAUUAGCGUUAGGUA where A at the 3' end is an adenosine added, or (2-A)                                         (SEQ ID NO: 12)
GGAUCGAAAGAUUUCCGCAUCCCCGAAAGGGUACAUGGCGUUAGGUA where A at the 3' end is an adenosine added.
(26) A process for preparing an acylated tRNA, comprising steps (a) to (e) below:
(a) providing two ribozymes for use in an immobilized form consisting of the RNA comprising a polynucleotide of the nucleotide sequence shown as (1-N) GGAUCGAAAGA-UUUCCGCGGCCCCGAAAGGGGAUUAGCG-UUAGGUN, where N at the 3' end is any nucleotide added or (1-A) GGAUCGAAAGAUUUCCGCGGC-CCCGAAAGGGGAUUAGCGUUAGGUA, where A at the 3' end is an adenosine added and the RNA comprising a polynucleotide of the nucleotide sequence shown as (2-N) GGAUCGAAAGAUUUCCGCAUC-CCCGAAAGGGUACAUGGCGUUAGGUN, where N at the 3' end is any nucleotide added or (2-A) GGAUCGAAA-GAUUUCCGCAUCCCCGAAAGGGUACAUG-GCGUUAGGUA, where A at the 3' end is an adenosine added, and immobilizing them to a support;
(b) providing a tRNA;
(c) synthesizing an esterified derivative or thioesterified derivative of a natural amino acid, nonnatural amino acid or lactic acid;
(d) contacting the ribozymes immobilized to the support with the tRNA and the esterified derivative of a natural amino acid, nonnatural amino acid or lactic acid to acylate the tRNA; and
(e) isolating the acylated tRNA.
(27) A kit capable of being used to obtain a tRNA molecule acylated with a natural amino acid, nonnatural amino acid, or lactic acid, comprising (a), (b) and (c) below:
(a) one or more ribozymes of the present invention;
(b) an esterified derivative or thioesterified derivative of a natural amino acid, nonnatural amino acid, or lactic acid used as a substrate for the ribozymes; and
(c) a tRNA.
(28) The kit of (27) wherein the ribozymes are immobilized to a support.
(29) A process for preparing a polypeptide containing any nonnatural amino acid or other carboxylic acid incorporated at a desired site, comprising steps (a) to (d) below:
(a) providing one or more ribozymes of the present invention;
(b) acylating a tRNA with a nonnatural amino acid or carboxylic acid using the ribozyme;
(c) providing an mRNA having a codon complementary to the anticodon of the tRNA at a desired site; and
(d) adding the acylated tRNA and the mRNA to a translation system to prepare a polypeptide containing the nonnatural amino acid or carboxylic acid incorporated at the desired site.
(30) The process of (29) wherein the carboxylic acid is lactic acid.
(31) The process of (29) or (30) wherein the tRNA has an anticodon corresponding to a stop codon, a four-base anticodon, an anticodon containing an artificial nucleotide, or an anticodon complementary to a codon encoding a natural amino acid.
(32) The process of (29) to (31), further comprising the step of separating the acylated tRNA from the ribozyme before it is added to a translation system in step (d).
(33) The process of (29) to (32) wherein the ribozyme is immobilized to a support.

ADVANTAGES OF THE INVENTION

By using the ribozymes of the present invention, all types of amino acids can be inexpensively, conveniently and rapidly attached to all tRNAs including artificial tRNAs. The ribozymes of the present invention can accept even carboxylic acids other than amino acids as acyl donor substrates. Moreover, one type of ribozyme molecule is compatible with various tRNAs/amino acids (carboxylic acids). Synthesis of substrates is very simple, and acylation reaction is also convenient.

According to the methods using the ribozymes of the present invention, all tRNAs can be aminoacylated because the recognition site is located at the 3' end having a tRNA consensus sequence. They can use tRNAs as substrates and therefore, they are compatible with various codons so that site-specific unnatural acid mutagenesis can be performed at will. Such features can be achieved by the ribozymes that are completely artificial catalysts.

BRIEF DESCRIPTION OF THE DRAWINGS

FIG. 7 schematically shows the secondary structures of Superflexizymes.
FIG. 8 shows the results of a streptavidin gel shift assay comparing Flexizyme and Superflexizyme 2 in the aminoacylation of a tRNA.

PREFERRED EMBODIMENTS OF THE INVENTION

Figure 1:
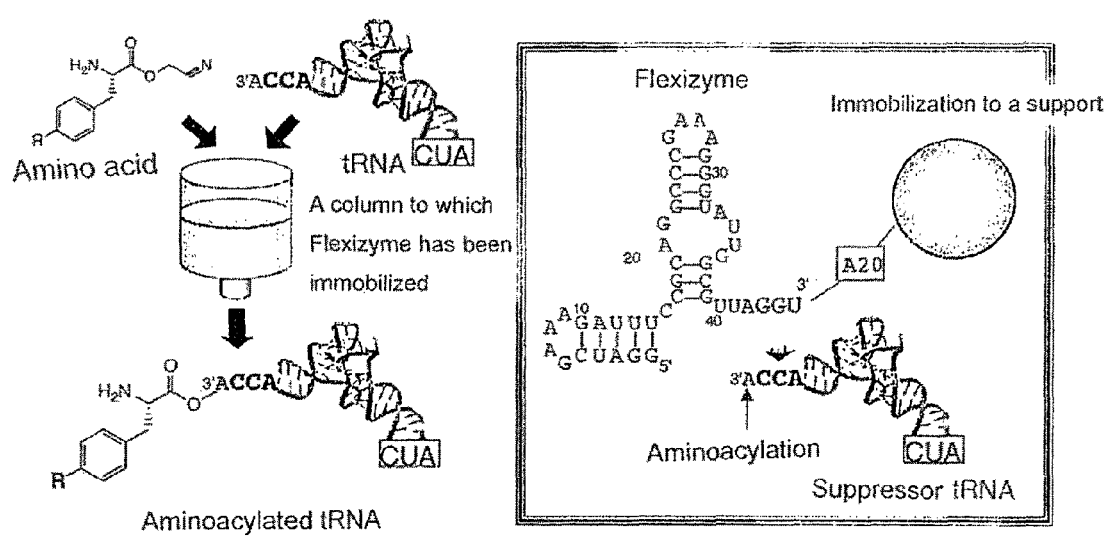
FIG. 1 shows a diagram of Flexizyme (Background Art).

For a better understanding of the present invention, terms used herein are explained before describing the invention in detail.

A "ribozyme" refers to an RNA molecule (RNA enzyme) capable of catalyzing a chemical reaction.

A "polynucleotide" refers to a polymer of at least 8 nucleotides in length selected from ribonucleotides, deoxyribonucleotides, or modified forms thereof.

A "ribonucleotide" refers to a nucleotide containing D-ribose as the sugar moiety and forming a component of RNA. The base moiety of a ribonucleotide consists of adenine, guanine, cytosine or uracil, and the respective ribonucleotides are called adenine nucleotide (A), guanine nucleotide (G), cytosine nucleotide (C), and uracil nucleotide (U). Conventional one-letter abbreviations corresponding to the respective ribonucleotides or bases are shown in parentheses.

A "base pair" refers to a specific combination of two nucleotides of nucleic acids connected via hydrogen bonds. A combination of nucleotides capable of forming a base pair are said to be "complementary" to each other. In DNA, adenine (A) pairs with thymine (T) and guanine (G) pairs with cytosine (C), while in RNA, A pairs with uracil (U) and G pairs with C. In RNA, so-called non-Watson-Crick base pairs such as G-A, G-U also occur as thermodynamically stable base pairs, and these combinations are also said to be "complementary" herein.

A "substrate" refers to a compound or molecule undergoing enzymatic catalysis. The acylation catalyst ribozymes of the present invention use tRNAs and amino acids and other carboxylic acids as substrates. However, the simple reference to "substrate" herein may exclusively mean various amino acids and other carboxylic acids in some contexts because the ribozymes of the present invention can accept any tRNA as their substrates.

A "tRNA" refers to both of a natural tRNA and an artificially constructed tRNA. It refers to an RNA molecule having a sequence corresponding to the formation of a secondary structure similar to the cloverleaf structure and further assuming a compact L-shaped tertiary structure in which an amino acid or other carboxylic acid is attached to the 3' end corresponding to one end of the L-shaped structure (acylation) while the codon on mRNA is recognized by the anticodon at the other end. Artificial tRNAs including minihelices and microhelices having more simplified structures are sometimes called "tRNA-like molecules" or "tRNA analogs".

A "natural amino acid" refers to any one of twenty amino acids that normally aminoacylate tRNAs in living cells. Such amino acids are α-aminocarboxylic acids (or substituted α-aminocarboxylic acids), including alanine (Ala), valine (Val), leucine (Leu), isoleucine (Ile), proline (Pro), tryptophan (Trp), phenylalanine (Phe), methionine (Met), glycine (Gly), serine (Ser), threonine (Thr), tyrosine (Tyr), cysteine (Cys), glutamine (Gln), asparagine (Asn), lysine (Lys), arginine (Arg), histidine (His), aspartic acid (Asp), and glutamic acid (Glu). Thus, a "nonnatural amino acid" refers to any amino acid other than the twenty natural amino acids mentioned above (or derivatives thereof). The nonnatural amino acid may be artificially synthesized or may naturally occur. The nonnatural amino acid here may also be a derivative of a natural amino acid.

An "amino acid" refers to a compound having two functional groups consisting of an amino group ($-NR_2$) and a carboxyl group ($-COOH$). For example, amino acids include nonnatural amino acids containing modified amino groups such as alkyl amino ($NH-R$) and acyl amino ($NH-CO-R$). Nonnatural amino acids also include β-amino acids, γ-amino acids, and δ-amino acids.

A "carboxylic acid" refers to a compound having a carboxyl group in the molecule, and especially in the present invention, hydroxycarboxylic acids (hydroxy acids) also having a hydroxyl group in the molecule are important. Examples thereof include lactic acid typified by an α-hydroxycarboxylic acid and lactic acid typified by a β-hydroxycarboxylic acid. It can be said that an amino acid is also one of carboxylic acids. As used herein, the term "carboxylic acid" is used to include amino acids unless otherwise noted.

A "tRNA acylation" means a process of attaching an acyl group ($R-CO-$) to a tRNA. In this process, an acyl group of an amino acid or other carboxylic acid is attached to a hydroxyl group (2' or 3'-OH) of ribose in a nucleotide at the 3' end of a tRNA via an ester bond.

An "acyl donor" or "acyl donor substrate" refers to a compound giving an acyl group in tRNA acylation. As used herein, it applies to amino acids and other carboxylic acids, which are compounds having an acyl group in the molecule.

A "polypeptide" refers to a series of two or more amino acids joined by peptide bonds. Peptide bonds (amide bonds) are covalent bonds between the carbon atom of the carboxyl group of a first amino acid and the nitrogen atom of the amino group of a second amino acid ($-CO-NH-$). As used herein, mutant polypeptides in which amino acids have been partially replaced by α-hydroxycarboxylic acids or β-hydroxycarboxylic acids are also sometimes called polypeptides. In this case, some bonds occur via linkage between a carboxyl group and a hydroxyl group ($-CO-O-$).

Unless otherwise specified, materials and procedures for carrying out the present invention are those described in various general textbooks and specialized documents and they are used according to conventional methods well-known in the technical field of chemistry and molecular biology. As for references in molecular biology, see e.g., Sambrook et al., Molecular Cloning: A Laboratory Manual, Second Edition, Cold Spring Harbor Laboratory Press, Cold Spring Harbor, N.Y. (1989); Ausubel et al., Current Protocols in Molecular Biology, Greene Publishing Associates (1992); and Harlow and Lane Using Antibodies: A Laboratory Manual, Cold Spring Harbor Laboratory Press, Cold Spring Harbor, N.Y. (1999).

Structure of tRNA

The ribozymes of the present invention (acylation RNA catalysts) catalyze tRNA acylation and have a recognition site at the 3' end containing a tRNA consensus sequence (RCCA-3' wherein R is a nucleotide A or G at position 73 called discriminator base). For a better understanding of the present invention, the structure of tRNA is explained below.

Figure 2:
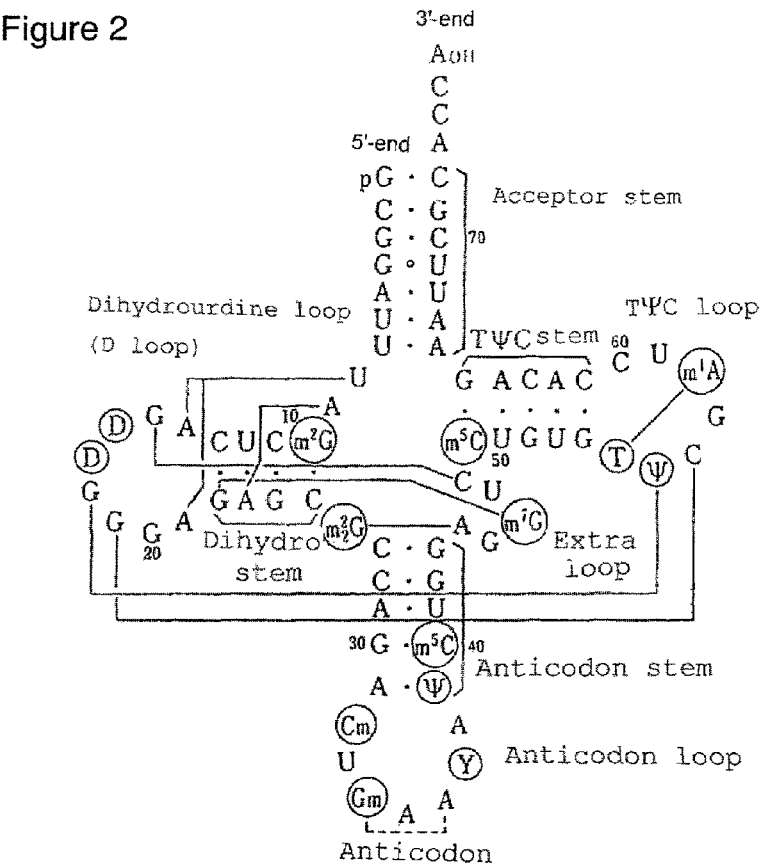
FIG. 2 shows a schematic diagram of tRNA ["(a) Cloverleaf structure of yeast phenylalanine tRNA" cited from "Dictionary of Biochemistry", K. Imabori and T. Yamakawa eds., page 897 (Third Edition, 1998, Tokyo Kagaku Dojin)].

Assembly of secondary structures from the previously determined nucleotide sequences of tRNAs leads to one common structure (FIG. 2). This structure is called "cloverleaf structure" by the similarity to a cloverleaf, and used as a model structure representing the secondary structures of tRNAs. The nucleotide chains corresponding to the stems of the clover form base pairs as double strands, and are called "stem". The nucleotide chains corresponding to the leaves do not form base pairs, and are called "loop". The structures combining a stem and a loop are called "arm", including anticodon arm, D arm, and TΦC arm. The tertiary structures of tRNAs are compact L-shaped structures in which each arms is further folded.

Regularity exists in size between each stem and loop. For example, the anticodon loop corresponding to the top leaf among the three leaves consists of seven nucleotides. The three-base sequence at the midpoint of the loop is the anticodon, which is involved in the recognition of codons. The stem leading to the leaf corresponding to the anticodon loop is the anticodon stem, which consists of 5 base pairs. The main stem of the clover is the acceptor stem, which consists of 7 base pairs. The 3' end of tRNA consists of a single strand of four residues, and the terminal three residues form a CCA sequence in all tRNAs and amino acids are attached to the 2'-OH or 3'-OH group of the terminal adenosine residue via an ester bond. The fourth base from the 3' end of tRNA (at position 73 adjacent to the 3'-terminal CCA sequence) is called discriminator base and involved in the amino acid specificity of tRNA.

The ribozymes of the present invention are designed to recognize the 3'-terminal consensus sequence (nucleotide sequence at positions 73-75) containing the discriminator base (A or G) of tRNAs.

Ribozymes of the Present Invention

The ribozymes of the present invention are artificial ribozymes constructed on the basis of "Flexizyme" explained in Background Art. Specifically, they were created by in vitro molecular evolution using an RNA pool consisting of sequences having a ribozyme domain obtained by partially randomizing the RNA sequence of Flexizyme and a tRNA domain added to the 3' end of the ribozyme domain. First, a suitable acyl donor substrate was added to the RNA pool to allow the reaction to proceed, thereby selecting active species capable of acylating the tRNA domain (intramolecular interactions). Activity was further evaluated in intermolecular interactions using sequences lacking the tRNA domain (the ribozyme domain) to select species capable of acylation with high efficiency as the ribozymes of the present invention. For general explanation about the creation of artificial ribozymes, see Protein, Nucleic acid and enzyme (Tanpakusitsu Kakusan Koso), Vol. 48 No. 11 (2003) 1511-1518.

Figure 3:
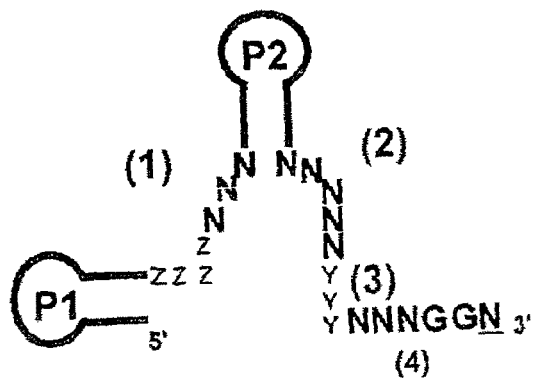
FIG. 3 schematically shows the secondary structure of a ribozyme of the present invention.

The secondary structure of the ribozymes of the present invention is shown in FIG. 3.

In FIG. 3, the domains represented by P1 and P2 are nucleotide sequence domains for fixing the two-dimensional structure of the ARS ribozyme in an active form and have a stem-loop structure. N each independently represents any monoribonucleotide of U, C, A and G, in which N(1) consists of 3 or 4 ribonucleotides; N(2) consists of 5 or 6 ribonucleotides; N(3) consists of 2 ribonucleotides; and N(4) consists of one ribonucleotide. Z or Y each independently represents C or G. N at the 3' end represents a monoribonucleotide complementary to the discriminator base A or G (the nucleotide at position 73) of tRNA, and selected from U, C, A and G.

Thus, the ribozymes of the present invention are ribozymes catalyzing tRNA acylation and having an RNA sequence represented by the following general formula (formula 1): (formula 1)

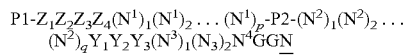

In formula 1, $(N^1)_1$-$(N^1)_p$ each independently represent any monoribonucleotide of U, C, A and G; p represents 3 or 4; $(N^2)_1$-$(N^2)_q$ each independently represent any monoribonucleotide of U, C, A and G; q represents 5 or 6; $(N^3)_1$-$(N^3)_2$ each independently represent any monoribonucleotide of U, C, A and G; $N^4$ represents any monoribonucleotide of U, C, A and G; $Z_1$-$Z_4$ each independently represent C or G; $Y_1$-$Y_3$ each independently represent C or G; $\underline{N}$ represents a monoribonucleotide complementary to A or G; U represents an uracil nucleotide; C represents a cytosine nucleotide; A represents an adenine nucleotide; G represents a guanine nucleotide; and P1 and P2 represent a domain consisting of any RNA sequence capable of having a stem-loop structure.

As previously described, when the ribozymes of the present invention recognize a tRNA, the 3' end containing a tRNA consensus sequence is used as the recognition site. In other words, the ribozymes recognize the 3' end of a tRNA to bind it via the 3'-terminal GGN motif. This is because the ribozymes were designed in such a manner that the GGN motif could be complementary to the nucleotide sequence at positions 73-75 at the 3' end of the tRNA binding the ribozymes. The nucleotide N forming a base pair with nucleotide 73 (discriminator base) of the tRNA is complementary to A or G, and can be mutated to be complementary to it depending on the type of the tRNA binding the ribozyme. A nucleotide complementary to A or G means a nucleotide capable of forming a base pair in a broad sense including non-Watson-Crick base pairs, where the nucleotide complementary to A is U or G, and the nucleotide complementary to G is C, A or U.

Next, the expression "P1 and P2 represent a domain consisting of any RNA sequence capable of having a stem-loop structure" is explained. P1 and P2 domains are nucleotide sequence domains defining the two-dimensional structures of the ARS ribozymes and have a stem-loop structure. A stem structure in the P1 and P2 domains means a structure preferentially assuming a double strand by forming a wholly or partially complementary base pair in the secondary sequence. A loop structure means any single strand in the form of a loop connecting stem structures. Loop structures having a short stable structure include four-base loops (tetraloops) typified by GAAA, GAGA, UUCG, etc. Stem-loop structures in the P1 and P2 domains include all nucleotide sequences capable of preferentially having a stem-loop structure without depending on the nucleotide sequence and the length of the stem or the size of the loop. However, an appropriate length in view of the overall size of the ribozyme should be desirably defined as an RNA sequence consisting of about 10-24 ribonucleotides for P1 or P2 in formula (1). The P1 and P2 domains are responsible for fixing the structure of the ribozyme in an active form, and the specific RNA sequence of the P1 or P2 domain may be any sequence capable of having a stem-loop structure. Such a sequence can be arbitrarily selected from known sequences, and as an example, an RNA sequence consisting of about 10-24 ribonucleotides can be illustrated as a secondary structure represented by the formula below.

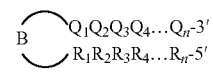

wherein B represents any single-stranded loop consisting of 1-8 ribonucleotides selected from U, C, A or G; $Q_1$-$Q_n$ and $R_1$-$R_n$ are segments of a stem structure, and $Q_1$-$Q_n$ each independently represent any monoribonucleotide of U, C, A and G and can preferentially assume a double-stranded structure by forming wholly or partially complementary base pairs with $R_1$-$R_n$. Therefore, the sequence of $R_1$-$R_n$ is complementary or partially complementary to the sequence of $Q_1$-$Q_n$. n represents an integer of 1-10.

A preferred example of B is a stable tetraloop. Preferred examples of stable tetraloops include GAAA, GAGA, UUCG, etc. For example, the specific RNA sequence of the P1 or P2 domain where the stable tetraloop is GAAA can be illustrated as a secondary structure represented by the formula below.

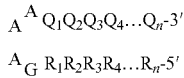

Alternatively, the specific RNA sequence of the P1 or P2 domain where the stable tetraloop is UUCG can be illustrated as a secondary structure represented by the formula below.

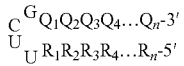

wherein $Q_1$-$Q_n$ each independently represent any monoribonucleotide of U, C, A and G; and $R_1$-$R_n$ each represent a monoribonucleotide complementary or partially complementary to $Q_1$-$Q_n$.

More specific examples of such sequences capable of assuming a stem-loop structure include, but not limited to, 5'-GGAUCGAAAGAUCC-3' (SEQ ID NO: 24) and 5'-CCCUUCGGGG-3' (SEQ ID NO: 25) where complementary nucleotide sequences are underlined.

The ribozymes of the present invention were created on the basis of "Flexizyme" by in vitro molecular evolution from an RNA pool prepared by randomly selecting nucleotides supposed to be important for the activity of Flexizyme. The general formula represented by formula (1) include the sequence of Flexizyme, in which the sequence of Z1-Z4 is CCGC, and the sequence of (N1)1-(N1)p is AGG, and the sequence of (N2)1-(N2)q is UAUUG, and the sequence of Y1-Y3 is GCG, and the sequence of (N3)1-(N3)2 is UU, and N4 is A, and the sequence of P1 is GGAUCGAAAGAUUU (SEQ ID NO: 5), and the sequence of P2 is CCCGAAAGGG (SEQ ID NO: 6).

The ribozymes of the present invention dramatically increased in the specificity for their acyl donor substrates and improved in activity over the original Flexizyme especially by changing the sequences represented by N("). Thus, an embodiment of the ribozymes of the present invention is a ribozyme catalyzing tRNA acylation and having a structure of (formula 1) above wherein $(N^1)_1$-$(N^1)_p$, $(N^2)_1$-$(N^2)_q$, $(N^3)_1$-$(N^3)_2$ and $N^4$ are RNA sequences of defined ribonucleotides. As a specific example in this case, $(N^1)_1$-$(N^1)_p$ is GGC, and $(N^2)_1$-$(N^2)_q$ is GAUUA, and $(N^3)_1$-$(N^3)_2$ is UU, and $N^4$ is A. As another specific example, $(N^1)_1$-$(N^1)_p$ is AUC, and $(N^2)_1$-$(N^2)_q$ is UACAUG, and $(N^3)_1$-$(N^3)_2$ is UU, and $N^4$ is A.

In another embodiment, the ribozymes of the present invention are ribozymes catalyzing tRNA acylation and having a structure of the RNA sequence of (formula 1) above wherein the ribonucleotides of $Z_1$-$Z_4$ and $Y_1$-$Y_3$ and $N^4$ are defined as represented by general formula (2) below.

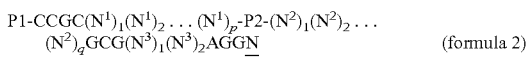

In formula 2, $(N^1)_1$-$(N^1)_p$ each independently represent any monoribonucleotide of U, C, A and G; p represents 3 or 4; $(N^2)_1$-$(N^2)_q$ each independently represent any monoribonucleotide of U, C, A and G; q represents 5 or 6; $(N^3)_1$-$(N^3)_2$ each independently represent any monoribonucleotide of U, C, A and G; U represents an uracil nucleotide; C represents a cytosine nucleotide; A represents an adenine nucleotide; G represents a guanine nucleotide; N represents a monoribonucleotide complementary to A or $\overline{G}$; and P1 and P2 represent a domain consisting of any RNA sequence capable of having a stem-loop structure.

In another embodiment, the ribozymes of the present invention are ribozymes catalyzing tRNA acylation and having a structure of the RNA sequence of formula (2) above wherein the ribonucleotides of $(N^1)_1$-$(N^1)_p$, $(N^2)_1$-$(N^2)_q$ and $(N^3)_1$-$(N^3)_2$ are further defined. Such an RNA sequence is represented by (I) or (II) below.

P1-CCGCGGC-P2-GAUUAGCGUUAGG$\underline{N}$ (I) (SEQ ID NOS: 1 and 2)

P1-CCGCAUC-P2-UACAUGGCGUUAGG$\underline{N}$ (II) (SEQ ID NOS: 3 and 4)

In formula (I) and (II), U represents a uracil nucleotide; C represents a cytosine nucleotide; A represents an adenine nucleotide; G represents a guanine nucleotide; $\underline{N}$ represents a monoribonucleotide complementary to A or G; and P1 and P2 represent a domain consisting of any RNA sequence capable of having a stem-loop structure.

In formula (I) or (II) above, the RNA sequences of the P1 domain and P2 domain can also be defined. In this case, P1 can be GGAUCGAAAGAUUU (SEQ ID NO: 5) and P2 can be CCCGAAAGGG (SEQ ID NO: 6). Alternatively, P1 can be GGAUCGAAAGAUUU (SEQ ID NO: 5), and P2 can consist of any RNA sequence. Alternatively, P1 can consist of any RNA sequence, and P2 can be CCCGAAAGGG (SEQ ID NO: 6).

The ribozymes of the present invention can also be ribozymes catalyzing tRNA acylation and consisting of any one of RNA sequences (a)-(d) below.

(a) (SEQ ID NO: 7)
GGAUCGAAAGAUUUCCGCGGC<u>CCCGAAAGGG</u>GAUUAGCGUUAGGU-3';

(b) (SEQ ID NO: 8)
GGAUCGAAAGAUUUCCGCAUC<u>CCCGAAAGGG</u>UACAUGGCGUUAGGU-3';

(c) an RNA sequence identical to sequence (a) except that U at the 3' end has been replaced by any nucleotide designed to be complementary to nucleotide 73 in the tRNA to be acylated;

(d) an RNA sequence identical to sequence (b) except that U at the 3' end has been replaced by any nucleotide designed to be complementary to nucleotide 73 in the tRNA to be acylated.

In formulae (a) and (b), the sequences corresponding to stem-loop structures are underlined, and the nucleotides at the tRNA-binding site are the 3'-terminal GGU motif. U represents a uracil nucleotide, C represents a cytosine nucleotide, A represents an adenine nucleotide, and G represents a guanine nucleotide.

The ribozyme consisting of the sequence of formula (a) (SEQ ID NO: 7) is named as Superflexizyme 1, and the ribozyme consisting of the sequence of formula (b) (SEQ ID NO: 8) is named as Superflexizyme 2, and they will be further explained in detail in the Examples below (FIG. 7). Superflexizymes 1 and 2 were created to have P1 and P2 domains and the 3'-terminal GGU motif as the tRNA recognition site approximately identical to those of the original Flexizyme. In addition, Superflexizyme 1 or 2 can be artificially altered into a ribozyme compatible with any tRNA by changing the GGU motif into a GGN motif (where N is any base complementary to and forming a base pair with the discriminator base at position 73 of tRNA). Thus, U at the 3' end can be replaced in the ribozyme sequences of (c) and (d) depending on the discriminator base of the tRNA to be acylated. It is understood that in the sequences of (a)-(d), the P1 domain (GGAUCGAAAGAUUU (SEQ ID NO: 5)) and P2 domain (CCCGAAAGGG (SEQ ID NO: 6)) can also be replaced by any other stem-loop structure.

Those skilled in the art can prepare a ribozyme of the present invention by synthesizing an RNA having a sequence as explained above. The synthesis of the RNA can be performed by any method commonly used by those skilled in the art. For example, it will be convenient to chemically synthesize a DNA corresponding to an RNA sequence forming a ribozyme of the present invention, amplify it by PCR to prepare a template DNA and transcribe it by T7RNA polymerase to synthesize an intended RNA.

A ribozyme for use in a form immobilized to a suitable support such as a resin can also be provided, comprising a nucleic acid molecule obtained by adding any one or more oxidatively modifiable nucleotides to a ribozyme RNA.

Thus, a polynucleotide comprising any one of nucleic acid molecules (a)-(d) below in their molecules in connection with an RNA molecule constituting a ribozyme of the present invention is also included in the present invention: (a) an RNA constituting a ribozyme of the present invention; (b) an RNA consisting of a sequence complementary to the RNA of (a) above; (c) a DNA consisting of a sequence identical to the RNA of (a) above, but U is replaced by T; (d) a DNA consisting of a sequence identical to the RNA of (b) above, but U is replaced by T.

Acyl Donor Substrates for the Ribozymes of the Present Invention

The ribozymes of the present invention ribozymes catalyzing the reaction of attaching natural amino acids, nonnatural amino acids, lactic acid, and other carboxylic acids to tRNAs via acyl groups, i.e., tRNA acylation. In this reaction, acyl moieties of natural amino acids, nonnatural amino acids, lactic acid, and other carboxylic acids are attached to a hydroxyl group (2' or 3'-OH) of ribose of the 3'-terminal nucleotide of tRNAs via ester bonds.

Practically, natural amino acids, nonnatural amino acids, lactic acid, and other carboxylic acids have been preliminarily converted into modestly activated esterified or thioesterified derivatives before they are contacted with a ribozyme, and the ribozymes of the present invention catalyze the reaction of transferring the acyl group of such modestly activated substrates to the 3' end of tRNA. Esterified or thioesterified derivatives of natural amino acids, nonnatural amino acids, lactic acid, and other carboxylic acids used as acyl donor substrates in this acylation reaction are explained in detail.

Figure 4:
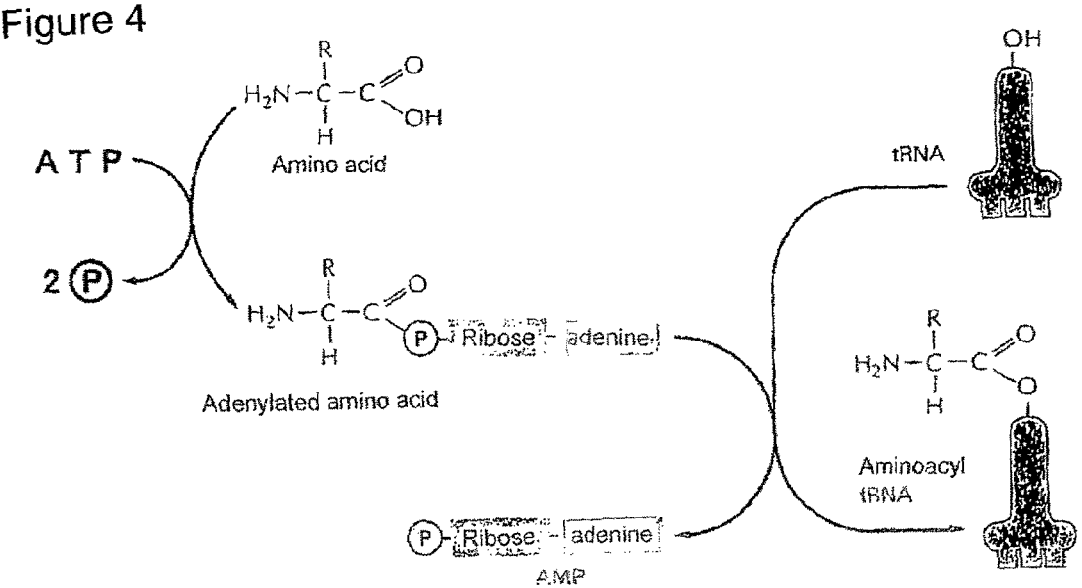
FIG. 4 shows aminoacylation reaction in nature ["FIG. 6-56 Activation of amino acids" cited from "MOLECULAR BIOLOGY OF THE CELL" by Alberts, Johnson, Lewis, Raff, Roberts, Walter, Japanese version by Keiko Nakamura and Kenichi Matsubara, page 339 (Fourth Edition, 2004, Newton Press)].

In nature, ARS protein enzymes catalyze a two-step reaction involving ATP hydrolysis and activation of a conjugated amino acid substrate followed by binding of the amino acid substrate to a tRNA to synthesize an aminoacyl-tRNA. First, the carboxyl group of an amino acid is activated by binding the AMP moiety to form an adenylated amino acid. Then, AMP detaches from the adenylated amino acid, and the carboxyl group of the amino acid is transferred to the hydroxyl group of the 3'-terminal ribose of the tRNA. By this transfer, the amino acid forms an activated ester bond with the tRNA, giving an aminoacylated tRNA (see FIG. 4). The ester bond between the activated amino acid and the tRNA is a high-energy bond releasing a large free energy by hydrolysis, and the energy of this bond is used to covalently link amino acids to extend the polypeptide chain during the subsequent step of protein synthesis.

However, both of the catalytic activities of the two-step reaction were not sought in the present invention, but the activation step was skipped by using preliminarily modestly activated substrates and, ribozymes catalyzing the reaction step of attaching a substrate such as an amino acid or lactic acid other carboxylic acid to a tRNA (acylation) were constructed. In other words, enzymatic adenylation is skipped and instead, a derivative of an amino acid or lactic acid or other carboxylic acid having a modestly activated ester bond is used as a substrate in the carbonyl group where acylation proceeds. Typically, the activation of an acyl group can be achieved by linking it via an ester bond to an electron-withdrawing leaving group, but esters having a too strong electron-withdrawing leaving group invite not only hydrolysis in water but also acylation to random RNAs. Thus, a modestly activated acyl donor must be used in order to prevent such side reactions. The ribozymes of the present invention can catalyze tRNA acylation by binding modestly activated esterified derivatives or the like of amino acids or lactic acid other carboxylic acids that would not undergo any reaction without catalyst. The activation of such ester bonds can be performed by using a cyanomethyl ester, a thioester, or a benzyl ester having a nitro group or fluorine or other electron-withdrawing functional groups. As used herein in reference to acyl donor substrates, an electron-withdrawing leaving group modestly activating an acyl group in this manner is called "acyl leaving group" or simply "leaving group".

To accept substrates having various side chains (amino acids and carboxylic acids), a strategy to optimize the substrates was needed. Preferred amino acid substrates used in the conventional Flexizyme were those having an aromatic group in the side chain. This results from the understanding that Flexizyme recognizes the aromatic ring in the side chain of an amino acid used as a substrate. Thus, substrates were optimized in the present invention so that the substrate recognition site could be located at the acyl leaving group of amino acid or lactic acid or other carboxylic acid substrates. This is based on the assumption that amino acids and carboxylic acids having various side chains can be accepted by locating the substrate recognition site at the leaving group to avoid recognition of the side chain by the ribozyme. Specifically, ribozymes having an aromatic ring at a site corresponding to the acyl leaving group (serving as a recognition site) were prepared and used for molecular evolution because the original Flexizyme seemed to recognize aromatic rings.

Figure 5:
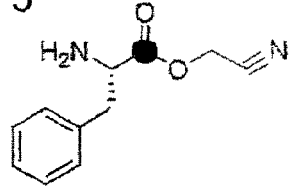
FIG. 5 illustrates the design of substrates.
Figure 5:
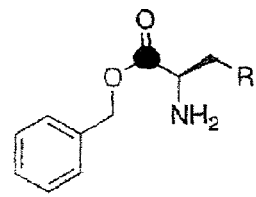

Referring to FIG. 5, an embodiment of a specific method for designing such a substrate is explained. The upper structural formula in FIG. 5 shows a cyanomethyl ester of an aromatic amino acid as an example of a conventional substrate, in which the original recognition site by Flexizyme is the aromatic ring moiety in the amino acid side chain:

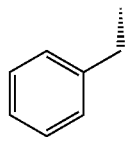

and the leaving group moiety (cyanomethyl moiety):

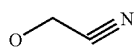

did not seem to be recognized by Flexizyme. This is because experimental results about conventional Flexizyme showed that various leaving groups such as AMP, thioesters, cyanomethyl esters were accepted. Thus, it was intended in the present invention to increase the number of compatible substrates to also cover substrates other than aromatic amino acids by switching the recognition site from the substrate side chain to the leaving group and the substrate side chain to the leaving group of conventional substrates.

Specifically, an aromatic ring was introduced into the recognition site serving as the leaving group because Flexizyme seemed to recognize aromatic rings. The lower structural formula in FIG. 5 shows a non-limitative example (a benzyl ester derivative of an amino acid). Here, the aromatic ring at the recognition site and the carbon at the reaction site (in red circle) are preferably positioned at approximately the same distance. On the other hand, the ester bond should be modestly activated by introducing an electron-withdrawing group into the leaving group. Examples of electron-withdrawing groups activating ester bonds of the aromatic group as a leaving group may include introduction of a plurality of nitro groups or fluorine atoms, or direct withdrawal of electrons from the α-carbon of a benzyl using fluorine atoms or cyano groups. Substrates can also be activated by using thioesters instead of esters.

In the Examples below, examples of substrates having a cyanomethyl ester (CME), 3,5-dinitrobenzyl ester (DBE) or p-chlorobenzyl thioester (CBT) (FIG. 6) are specifically shown, but the present invention is not limited to them. Leaving group capable of sufficiently activating ester bonds with high reaction efficiency can be screened and used as appropriate.

Synthesis of esterified derivatives of amino acids or other carboxylic acids optimized to recognize leaving groups can be performed as follows.

Amino acid substrates are synthesized by first (1) reacting a Boc-protected amino acid with a compound having a halogen at the benzyl position and an electron-withdrawing group in the aromatic group to form an ester. Then, The Boc protective group is removed with an acid to synthesize an amino acid substrate. This ester can also be synthesized by (2) condensing a Boc-protected amino acid with a compound having a hydroxyl group at the benzyl position and an electron-withdrawing group in the aromatic group using a conventional condensing agent. It can also be synthesized by (3) mixing an activated Boc-protected amino acid with a compound having a hydroxyl group at the benzyl position and an electron-withdrawing group in the aromatic group. Among the three methods above, (1) is convenient and amino acid substrates were synthesized by using method (1) in the Examples below. Carboxylic acid substrates are synthesized in the same manner, but the deprotection with an acid in the synthetic pathway above because no amine exists.

Thioesters can be synthesized by using method (2) or (3) above. However, a compound having a thiol group at the benzyl position is used in place of the compound having a hydroxyl group at the benzyl position and an electron-withdrawing group in the aromatic group. The electron-withdrawing group in the aromatic group is not always needed because thioesters have relatively high activity. Of the two methods above, method (2) was used in the Examples below because it is relatively convenient.

For the synthesis of cyanomethyl esters of amino acids having an aromatic ring as a side chain among conventional substrates, see JPA 2005-528090 (WO2003-70740).

We used one specific acyl donor substrate for molecular evolution of acylation catalytic RNAs, thereby demonstrating that ribozymes compatible with not only the specific acyl donor substrate but also a wide range of other acyl donor substrates can be obtained. For example, molecular evolution of a cyanomethyl ester of phenylalanine (Phe-CME) as a conventional substrate or a dinitrobenzyl ester of hydroxybutyric acid (HBi-DBE) as a substrate containing an aromatic ring in the acyl leaving group yielded ribozymes compatible with the twenty natural amino acids and 9 or more nonnatural amino acids and lactic acid. In addition to esterified or thioesterified derivatives of amino acids having an aromatic ring in the side chain used as preferred substrates in conventional Flexizyme, the ribozymes of the present invention can also use esterified derivatives of amino acids having an aromatic ring in the acyl leaving group, thioesterified derivatives of amino acids having an aromatic ring in the acyl leaving group, esterified derivatives of lactic acid having an aromatic ring in the acyl leaving group, etc. This characteristic made the ribozymes compatible with the derivatives having any structure in the side chain. In some examples of the ribozymes of the present invention, activity toward cyanomethyl esters of amino acids having an aromatic ring in the side chain also improved over conventional Flexizyme.

Thus, acyl donor substrates for the ribozymes of the present invention are derivatives of hydroxycarboxylic acids (e.g., amino acids or lactic acid) having a modestly activated ester bond in the acyl leaving group and an aromatic ring in the side chain or acyl leaving group.

Acylation Reaction of tRNAs Using the Ribozymes of the Present Invention

Employing the ribozymes of the present invention, all amino acids can be used as substrates in the acylation of tRNAs. Thus, the 17 natural amino acids other than phenylalanine, tyrosine and tryptophan that could not be used as substrates for conventional Flexizyme can also be used as well as nonnatural amino acids having a side chain other than aromatic rings. Additionally, the ribozymes of the present invention can use carboxylic acids having a hydroxyl group in place of the amino group, e.g., lactic acid. This is one of important features of the ribozymes of the present invention, which is unimaginable from conventional ARSs and contrary to the common knowledge in biology. ARSs are enzymes for attaching a specific amino acid to its cognate tRNA (i.e., acylating a tRNA with an amino acid or aminoacylating a tRNA), whereby the genetic code of mRNA is translated into an amino acid. However, the ribozymes of the present invention can attach even hydroxycarboxylic acids other than amino acids to tRNAs (i.e., acylate tRNAs with carboxylic acids). Consequently, genetic codes can be translated into all amino acids including nonnatural amino acids and even hydroxycarboxylic acids.

Moreover, the ribozymes of the present invention are characterized in that they can induce acylation reactions with all tRNAs. This results from the fact that the site at which the ribozymes of the present invention recognize a tRNA to bind it (tRNA recognition site) requires only the 3'-terminal GGN motif, whereby GG in this GGN motif recognizes the 3'-terminal consensus sequence CC for all tRNA molecules and U recognizes the fourth discriminator base from the 3' end (in other words, N is a nucleotide complementary to the discriminator base of tRNAs). This is a remarkable difference from natural protein ARS enzymes or enzymes obtained by altering natural ARS enzymes. Natural ARSs sense various characteristics of tRNAs and strictly recognize only specific tRNAs because of a wide range of structural and chemical complementarity to tRNAs. In contrast, the ribozymes of the present invention recognize tRNAs to bind them by the complementarity between nucleotides of the GGN motif at the tRNA recognition site and the consensus sequence on the tRNA acceptor stem.

The ribozymes of the present invention were constructed on the basis of conventional parent Flexizyme, and contain a GGN motif as the tRNA recognition site, and P1 and P2 domains. P1 and P2 domains consist of a stem-loop structure for retaining sequences necessary for catalytic activity. Sequences necessary for catalytic activity include sites necessary for substrate recognition and acyl transfer reaction.

Accordingly, the ribozymes of the present invention comprise a GGN motif constituting the tRNA recognition site, P1 and P2 domains for fixing the structure, a substrate-binding site capable of recognizing an acyl donor substrate to bind it, and a catalytic activity site having the activity of catalyzing an acyl transfer reaction from the acyl donor substrate to a tRNA. Such a configuration allows the ribozymes to bind a tRNA as well as an acyl donor substrate, thereby catalyzing an acyl transfer reaction from the acyl donor substrate to the tRNA to specifically attach an acyl group to the 3' end of the tRNA, i.e., acylate the tRNA.

When the ribozymes of the present invention bind a tRNA and an acyl donor substrate to acylate the tRNA, the tRNA recognition site (the 3'-terminal GGN) of the ribozymes bind the tRNA via complementary base pairing. At the same time, the ribozymes of the present invention recognize the preliminarily modestly activated acyl donor substrate to bind it. During then, the ribozymes of the present invention seem to recognize the aromatic ring moiety in the side chain or acyl leaving group of the acyl donor substrate. An acyl transfer reaction from the acyl donor substrate to the 3' end of the tRNA seems to rapidly occur via correct binding of the acyl donor substrate and the tRNA on the ribozymes. During the acyl transfer reaction from the acyl donor substrate to the 3' end of the tRNA, the acyl leaving group of the substrate detaches and the acyl group is transferred to the hydroxyl group of the 3'-terminal ribose of the tRNA. By this transfer, an amino acid or hydroxycarboxylic acid forms an active ester bond with the tRNA to give an acylated tRNA. When the acylated tRNA is produced, the ribozymes detach from the product and become ready to bind a fresh enzyme.

Thus, the ribozymes of the present invention can be characterized as follows.

A ribozyme catalyzing tRNA acylation, comprising:
(a) a tRNA-binding site recognizing a tRNA to bind it;
(b) an acyl donor substrate-binding site recognizing an acyl donor substrate having a modestly activated ester bond in the acyl leaving group moiety and having an aromatic ring in the side chain or the acyl leaving group to bind it; and
(c) a catalytic activity site having an activity of catalyzing an acyl transfer reaction from the acyl donor substrate to the 3' end of the tRNA;
wherein the tRNA-binding site consists of the 3'-terminal GGU motif the ribozyme and said GGU motif is complementary to a nucleotide sequence RCC at positions 73-75 (where R is a discriminator base G or A) of the acyl acceptor stem portion at the 3' end of the tRNA binding the ribozyme, whereby the ribozyme binds the acyl acceptor stem portion at the 3' end of the tRNA via base pairing, thus rapidly inducing an acyl transfer reaction from the acyl donor substrate bound to the acyl donor substrate-binding site to the 3' end of the tRNA, and
wherein the nucleotide U on the ribozyme forming a base pair with nucleotide 73 (discriminator base) of the tRNA is complementary to A or G and can be mutated to be complementary to it depending on the type of the tRNA, whereby the ribozyme can acylate any tRNA.

The ribozymes of the present invention seem to recognize an aromatic ring on the substrate molecule. Thus, the acyl donor substrate has an aromatic ring in the side chain or an aromatic ring in the acyl leaving group.

The acyl donor substrate having an aromatic ring in the acyl leaving group can be represented by the general formula below.

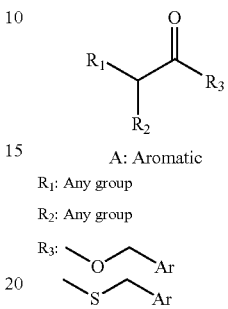

A: Aromatic
$R_1$: Any group
$R_2$: Any group
$R_3$:

wherein R1, R2, R3 represent any chemical structure. For example, R1 represents a chemical structure corresponding to nucleophilic functional groups such as amino, hydroxyl and thiol; R2 represents a chemical structure corresponding to side chain functional groups such as alkyl and aryl.
R3 represents a leaving group, especially a benzyl ester or thiobenzyl ester containing an aryl group (Ar) having an electron-withdrawing functional group. The acyl donor substrate-binding site of the ribozyme recognizes the leaving group ($R_3$) moiety of the substrate, whereby the ribozyme can acylate the tRNA with a carboxylic acid having any side chain as the acyl donor substrate.

Specific examples of acyl donor substrates having an aromatic ring in the acyl leaving group include esterified derivatives of amino acids having an aromatic ring in the acyl leaving group, thioesterified derivatives of amino acids having an aromatic ring in the acyl leaving group, and esterified derivatives of lactic acid having an aromatic ring in the acyl leaving group.

Synthesis of Acylated tRNAs Using the Ribozymes of the Present Invention

The ribozymes of the present invention can be used to synthesize tRNAs acylated with a desired acyl donor substrate.

A process for preparing an acylated tRNA using a ribozyme of the present invention comprises the steps of:
(a) providing one or more ribozymes of the present invention;
(b) providing a tRNA; (c) synthesizing a modestly activated carboxylic acid; (d) contacting the ribozyme with the tRNA and the modestly activated carboxylic acid to acylate the tRNA; and (e) isolating the acylated tRNA.

In this process, a preliminarily modestly activated carboxylic acid is used as an acyl donor substrate. The carboxylic acid used as an acyl donor substrates is e.g., a natural amino acid, a nonnatural amino acid, or lactic acid. Modest activation is achieved out by introducing an acyl leaving group capable of modestly activating an ester bond. Examples of modestly activated carboxylic acids include esterified derivatives of amino acids, thioesterified derivatives of amino acids, or esterified derivatives of carboxylic acids. Preferred examples of such acyl donor substrates include esterified derivatives or thioesterified derivatives of amino acids or lactic acid such as cyanomethyl esters of natural amino acids or nonnatural amino acids having an aromatic ring in the side chain, 3,5-dinitrobenzyl esters of natural amino acids or nonnatural amino acids, 4-chlorobenzyl thioesters of natural amino acids or nonnatural amino acids, cyanomethyl esters of phenyllacetic acid, and 3,5-dinitrobenzyl esters of phenyllacetic acid or alkyllactic acid.

In the process for preparing an acylated tRNA using a ribozyme of the present invention, any tRNA can be used. The tRNA may be a natural tRNA or an artificially constructed tRNA, so far as it is an RNA molecule having a sequence corresponding to the formation of a secondary structure similar to a cloverleaf structure and further forming an L-shaped three-dimensional structure in which an amino acid or other carboxylic acid is attached to the 3' end corresponding to one end (acylation) while the codon on mRNA is recognized by the anticodon at the other end. The Examples below describe acylation of tRNA$^{Asn}_{CUA}$, which is one of artificial suppressor tRNAs compatible with amber stop codons.

Acylation reaction of tRNAs using the ribozymes of the present invention can be performed in solution or on a column containing a ribozyme immobilized to a support. On a small scale of translation reaction of 100 µl or less, for example, tRNA acylation by a ribozyme may be performed in solution and a pellet precipitated with ethanol from the reaction solution may be dissolved in a suitable buffer (e.g., 1 mM potassium acetate, pH 5, etc.) and added to a translation system. For examples of small scale reaction conditions, see the procedure described in Example 3. Typical reaction conditions include reacting the following components at final concentrations: a tRNA at 0.5-20 µM, a ribozyme of the present invention at 0.5-20 µM, an acyl donor substrate at 2-10 mM, and 0.1 M Reaction Buffer containing 0.6 M $MgCl_2$, pH 7.5 at 0° C. for 1 hour-24 hours.

When the scale of translation reaction exceeds 100 µl, it is more convenient to use a ribozyme immobilized to a support with recycling the ribozyme in mind. Supports that can be used include, but not limited to, resins, agarose, Sepharose, magnetic beads, etc. The reaction using a ribozyme immobilized to a support can be performed according to e.g., the method described in Murakami, H., Bonzagni, N. J. and Suga, H. (2002). "Aminoacyl-tRNA synthesis by a resin-immobilized ribozyme." J. Am. Chem. Soc. 124(24): 6834-6835. The reaction product acylated tRNA can be isolated by various methods. An example is elution from the column with a buffer containing about 10 mM EDTA. The resin to which the ribozyme is immobilized can be recycled over ten times by equilibration with Reaction Buffer, for example.

In this manner, the ribozymes of the present invention simplify acylation reaction and can be combined with a substrate to provide a kit for obtaining an acylated tRNA. The kit may comprise at minimum (a) one or more ribozymes of the present invention (which may be immobilized to a support), (b) an esterified derivative or thioesterified derivative of a natural amino acid, nonnatural amino acid, or lactic acid serving as a substrate for the ribozyme(s); and (c) a tRNA, and optionally a reaction buffer, a reaction container, instructional materials, etc.

Superflexizyme-Mediated Synthesis of Acylated tRNAs

Of the ribozymes of the present invention, Superflexizyme 1 is compatible with amino acids having a cyanomethyl group as a leaving group and an aromatic ring as a side chain, similarly to the original Flexizyme. It also has activity toward amino acids having 4-chlorobenzyl thiol as a leaving group and a side chain other than aromatic rings. Especially, it is useful in that it has activity toward amino acids having a β-branched side chain (e.g., valine and isoleucine) in combination with 4-chlorobenzyl thiol. Moreover, it also shows activity toward phenyllactic acid or alkyllactic acid derivatives activated with cyanomethyl or 4-chlorobenzyl thiol.

Superflexizyme 2 has activity toward amino acids having 3,5-dinitrobenzyl alcohol as a leaving group and a side chain other than aromatic rings. This ribozyme is characterized in that it can retain activity toward the acyl donors even at lower concentrations (1 mM) as compared with other ribozymes. Moreover, 3,5-dinitrobenzyl alcohol is weak as an active group so that aminoacylation of non-specific tRNAs without catalyst can be completely avoided. However, Superflexizyme 2 has drawbacks such as low activity toward amino acids having 4-chlorobenzyl thiol as a leaving group as compared with Superflexizyme 1 and low activity toward amino acids having 3,5-dinitrobenzyl alcohol as a leaving group and a β-branched side chain.

Thus, amino acids having substantially any side chain can be covered by combining these two Superflexizymes. In general, amino acids having no β-branched side chain can be covered by using Superflexizyme 2 for acyl donors having 3,5-dinitrobenzyl alcohol as a leaving group. Amino acids having a β-branched side chain can be covered by using Superflexizyme 1 for acyl donors having 4-chlorobenzyl thiol as a leaving group.

Thus, a process for preparing a tRNA acylated with any amino acid or hydroxycarboxylic acid is provided by using Superflexizyme 1 and 2 in combination as follows.

A process for preparing an acylated tRNA, comprising steps of:

(a) providing two ribozymes catalyzing tRNA acylation, consisting of RNA sequences (1) and (2) below, respectively:

```
                                              (SEQ ID NO: 7)
(1) GGAUCGAAAGAUUUCCGCGGCCCCGAAAGGGGAUUAGCGUUAGGU,
and (SEQ ID NO: 8)
(2) GGAUCGAAAGAUUUCCGCAUCCCCGAAAGGGUACAUGGCGUUAGGU
```

(b) providing a tRNA;

(c) synthesizing an esterified derivative or thioesterified derivative of a natural amino acid, nonnatural amino acid or lactic acid;

(d) contacting the ribozymes with the tRNA and the natural amino acid, nonnatural amino acid or lactic acid to acylate the tRNA; and (e) isolating the acylated tRNA.

The two Superflexizymes can be each immobilized to a support. For immobilization, it is convenient to use Superflexizymes for use in an immobilized form, consisting of an RNA comprising a polynucleotide of nucleotide sequence (1-N) or (2-N) below having any oxidatively modifiable nucleotide added to the 3' end of the catalytic RNA molecule:

```
(1N)                                          (SEQ ID NO: 9)
GGAUCGAAAGAUUUCCGCGGCCCCGAAAGGGGAUUAGCGUUAGGUN
``` where N at the 3' end is any nucleotide added, or

```
(2-N)                                         (SEQ ID NO: 10)
GGAUCGAAAGAUUUCCGCAUCCCCGAAAGGGUACAUGGCGUUAGGUN
``` where N at the 3' end is any nucleotide added.

When the nucleotides N is adenosine, Superflexizymes for use in an immobilized form are used consisting of an RNA comprising a polynucleotide of nucleotide sequence (1-A) or (2-A) below:

(1-A)                                                    (SEQ ID NO: 11)
GGAUCGAAAGAUUUCCGCGGCCCCGAAAGGGGAUUAGCGUUAGGUA where A at the 3' end is an adenosine added, or (2-A)                                                    (SEQ ID NO: 12)
GGAUCGAAAGAUUUCCGCAUCCCCGAAAGGGUACAUGGCGUUAGGUA where A at the 3' end is an adenosine added.

When such a ribozyme for use in an immobilized form is used, a process for preparing an acylated tRNA comprises steps (a) to (e) below:
(a) providing two ribozymes for use in an immobilized form consisting of an RNA comprising a polynucleotide of the nucleotide sequence shown as (1-N) or (1-A), and (2-N) or (2-A), respectively, and immobilizing them to a support;
(b) providing a tRNA;
(c) synthesizing an esterified derivative or thioesterified derivative of a natural amino acid, nonnatural amino acid or lactic acid;
(d) contacting the ribozymes immobilized to a support with the tRNA and the esterified derivative of a natural amino acid, nonnatural amino acid or lactic acid to acylate the tRNA; and
(e) isolating the acylated tRNA.

Synthesis of Site-Specifically Mutated Polypeptides Using the Ribozymes of the Present Invention Polypeptides containing any nonnatural amino acid or hydroxycarboxylic acid incorporated into a desired site can be prepared by using a suitable suppressor tRNA charged with the nonnatural amino acid or hydroxycarboxylic acid.

For a better understanding of the present invention, the term suppressor tRNA or suppression is explained here. Typically, a suppressor tRNA is a tRNA that suppresses a trait mutation caused by a nucleotide substitution, insertion or deletion resulting from a gene mutation. In nature, many suppressor tRNAs are found in prokaryotes. They include tRNAs having acquired the ability of recognizing a stop codon produced by nucleotide substitution or the like in the translated region on mRNA as a codon corresponding to an amino acid (nonsense suppressor tRNAs) or the ability of reading a codon corresponding to an amino acid as a codon for another amino acid (missense tRNAs), and they can produce the original gene product or restore an altered function of the gene product (suppression). They also include tRNAs capable of suppressing a shift in the reading frame of a genetic code caused by a nucleotide insertion or deletion (frameshift suppressor tRNAs). Some frameshift suppressor tRNAs read four bases as a codon for an amino acid. In unnatural amino acid mutagenesis, a nonnatural amino acid is incorporated into the position of an amber codon (TAG) on a mutant gene by suppressing the amber codon using a suppressor tRNA aminoacylated with the nonnatural amino acid.

By using the ribozymes of the present invention, suitable suppressor tRNAs charged with various nonnatural amino acids can be readily synthesized. Moreover, suppressor tRNAs charged with hydroxycarboxylic acids can also be synthesized.

Thus, a process for preparing a site-specifically mutated polypeptide using a ribozyme of the present invention comprises the steps of: (a) providing a ribozyme of the present invention, (b) acylating a tRNA with a nonnatural amino acid or hydroxycarboxylic acid using the ribozyme, (c) providing an mRNA having a codon complementary to the anticodon of the tRNA at a desired site, and (d) adding the acylated tRNA and the mRNA to a translation system to prepare a polypeptide containing the nonnatural amino acid or carboxylic acid incorporated at the desired site. For details of each step, see the foregoing explanation. Matters especially related to the preparation of polypeptides are explained below.

When the ribozymes of the present invention are used to acylate a tRNA with a nonnatural amino acid or hydroxycarboxylic acid, the nonnatural amino acid can be principally any nonnatural amino acid. The ribozymes of the present invention can charge a tRNA with not only a nonnatural amino acid but also an α-hydroxycarboxylic acid or a β-hydroxycarboxylic acid to synthesize mutant polypeptides containing these carboxylic acids at a desired site.

Specific procedures for protein synthesis can be performed basically as described in Murakami, H., Kourouklis, D. and Suga, H. (2003). "Using a solid-phase ribozyme aminoacylation system to reprogram the genetic code." Chem. Biol. 10(11): 1077-84, but various modifications can be added. Typically, protein synthesis can be performed as follows.

The translation system used is preferably a cell-free translation system that uses a cell extract to synthesize a protein. This system allows for more artificial manipulations because it does not use a cell itself. Such a system typically contains ribosomal proteins, ribosomal RNAs, amino acids, tRNAs, GTP, ATP, translation initiation and extension factors, and other factors necessary for translation, and known such systems with high efficiency include *E. coli* cell extracts and wheat malt extracts. These produce several hundred micrograms to several milligrams/mL of protein by continuous supplying energy under dialysis. Some systems contain RNA polymerases for initiating transcription from gene DNA as well. *E. coli*-derived systems include RTS-100® from Roche Diagnostics and PURESYSTEM® from PGI and systems based on wheat malt extracts are available from ZoeGene Corporation, etc.

Alternatively, unnatural amino acid mutagenesis can be performed in a cell by introducing an aminoacylated suppressor tRNA into the cell. For example, a protein containing a nonnatural amino acid can be expressed in a cell by introducing a suitable suppressor tRNA aminoacylated by the method of the present invention via microinjection or transfection into *Xenopus* oocytes or mammalian cells.

The tRNA used is in orthogonal relation with natural ARSs present in the translation system. A tRNA in orthogonal relation with natural ARSs refers to a suppressor tRNA that is not aminoacylated by natural ARSs present in the translation system but can efficiently suppress the codon at a mutated site in the ribosome to express a desired nonnatural amino acid or carboxylic acid. For example, a natural amber suppressor tRNA derived from a different species can be used as such a tRNA. Alternatively, an artificially constructed tRNA can be used as such a tRNA. An example of an artificially constructed tRNA is an otRNA (orthogonal tRNA). This is an artificial tRNA derived from the amber suppressor tRNA$^{Asn}_{CUA}$ of *E. coli* and containing a G73A mutation, which is not aminoacylated in the *E. coli* translation system because it is not recognized by the *E. coli* ARS due to several artificial alterations. Alternatively, naturally derived tRNA-like molecules such as an amber suppressor tRNA derived from a species different from that of an extracellular translation system (e.g., human) can be used for this purpose.

The tRNA used as a substrate for the ribozymes of the present invention can be selected at will, and therefore, an optimal suppressor tRNA for the protein synthesis system used can be selected at will. This is a great advantage over existing ARS protein enzymes. ARS protein enzymes often show strict recognition for tRNAs and can use only tRNAs having a structure recognized by the enzymes. In contrast, the ARS ribozymes of the present invention can use all tRNAs as their substrates. The ribozymes of the present invention recognize a tRNA consensus sequence, but not the anticodon. Thus, versatile artificial tRNAs can also be provided, which share a common structure but only the anticodon loop varies to suit each desired substrate.

Preferred suppressor tRNAs are screened depending on the protein expression system. Screening can be performed as follows. First, tRNAs that are not aminoacylated by ARS protein enzymes endogenous to the protein expression system used. If tRNAs were aminoacylated by endogenous protein enzymes, other amino acids would be introduced into the site at which a nonnatural amino acid or hydroxycarboxylic acid is to be introduced. The acylated tRNA added must be efficiently incorporated into the ribosome of the protein expression system used. For this screening, tRNAs acylated by the ribozymes of the present invention can be used. As described previously, the tRNA recognition site of the ribozymes of the present invention is designed to recognize only the 3'-terminal consensus sequence of tRNAs. Thus, various tRNAs can be aminoacylated by the ribozymes of the present invention and used as screening samples.

For preparing a polypeptide containing a nonnatural amino acid or hydroxycarboxylic acid at a desired site, the incorporation site should be designated on mRNA. For this purpose, a codon encoding a nonnatural amino acid or hydroxycarboxylic acid is required in addition to a codon encoding a natural amino acid. On the other hand, a suitable suppressor tRNA having an anticodon complementary to that codon and charged with a desired nonnatural amino acid or hydroxycarboxylic acid is prepared as described above. When these are added to a translation system, the codon on the mRNA is recognized by the tRNA having the anticodon in the ribosome, whereby the nonnatural amino acid or hydroxycarboxylic acid is incorporated into a growing polypeptide chain.

A strategy to encode a nonnatural amino acid or hydroxycarboxylic acid is to assign a codon encoding no amino acid in the conventional genetic code table, i.e., to expand the codon encoding a pair of a genetic code and an amino acid. For example, any of the amber suppressor strategy using an anticodon corresponding to a stop codon, the four-base anticodon strategy, or the incorporation of an artificial nucleotide can be used. Moreover, a nonnatural amino acid can also be encoded by a codon consisting of more than four bases (e.g., five or more base codons).

As an example of codon expansion, a mutant polypeptide containing a nonnatural amino acid substituted for the amino acid at position 50 can be synthesized by adding an mRNA having a codon mutation at position 50 and a suppressor tRNA having a complementary anticodon aminoacylated with the nonnatural amino acid to a translation system. For example, when an amber codon (UAG) is used as a mutant codon, $tRNA^{Asn}_{CUA}$ can be used as a suppressor tRNA having a complementary anticodon, or when the mutant codon is a four-base codon (GGGU), $tRNA^{Asn}_{ACCC}$ is used. The mRNA can be prepared by transcription from a template DNA designed to contain a mutant codon at position 50. Alternatively, a mutant polypeptide can also be synthesized by adding a template DNA encoding an mRNA having a codon complementary to the anticodon of an aminoacylated suppressor tRNA to a system combining transcription and translation, instead of preparing an mRNA and then adding it to a translation system.

The artificially expanded codons can be determined at will, and a tRNA having a complementary anticodon can be charged with any nonnatural amino acid or hydroxycarboxylic acid by using the ribozymes of the present invention. As a result, multiple selectively mutated polypeptides can be synthesized from one mutant gene depending on the type of the tRNA used.

EXAMPLES

The following examples further explain in detail the invention described above, but they are given for illustrative purposes only and should not be construed to limit the scope of the present invention. Various changes or modifications can be made by those skilled in the art in the light of the description of the specification and the appended claims, and are included within the present invention.

Example 1

This embodiment describes the design and synthesis of substrate molecules.

Figure 6:
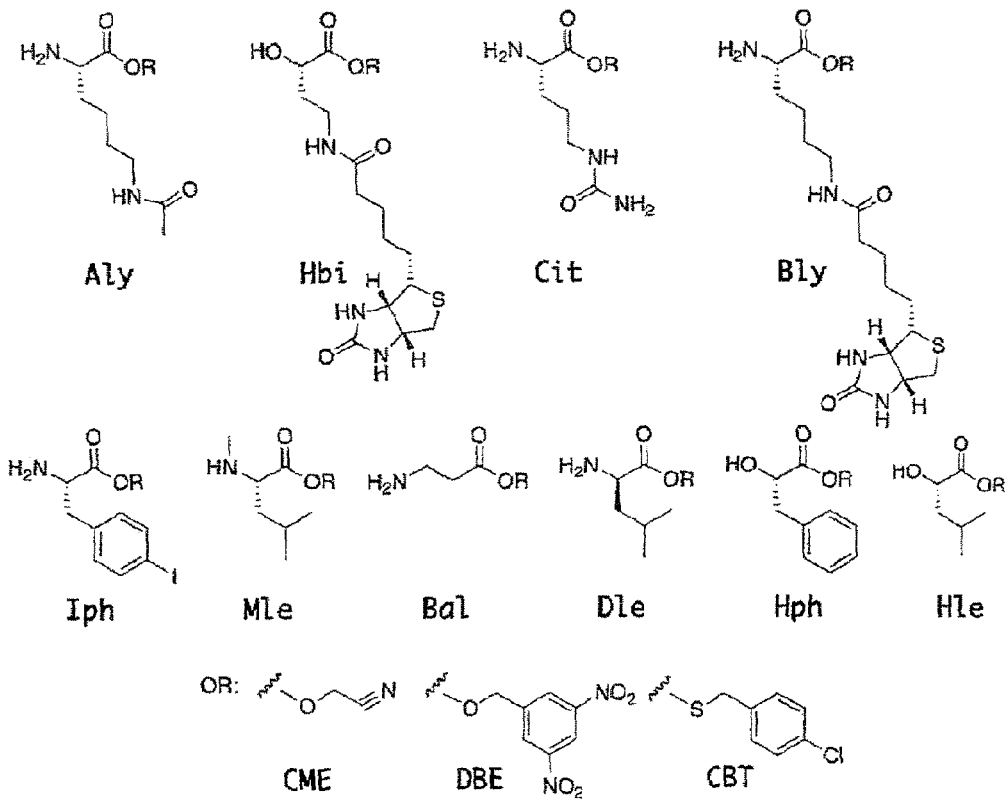
FIG. 6 shows exemplary substrates (amino acids, carboxylic acids) and leaving groups.

In this embodiment, substrate molecules were synthesized. Each substrate was designed to allow for acylation with any amino acid or lactic acid by altering the ribozyme recognition site from the side chain to the leaving group of the substrate molecule (FIG. 6). An aromatic group was used as the leaving group and ester bonds were activated using a thioester (CBT: p-chloral-benzyl thioester) or an ester having an electron-withdrawing functional group in the aromatic group (DBE: 3,5-dinitrobenzyl ester). Substrates having an aromatic group in the side chain were activated by a cyanomethyl ester (CME) as conventionally.

Synthesis of substrates having a CBT is shown below. First, N,N-bis(2-oxo-3-oxazolidinyl)phosphonic chloride (127 mg, 0.5 mmol) and a Boc amino acid (0.6 mmol) and triethylamine (150 mg, 1.5 mmol) were added to dichloromethane (3 mL). To this mixture was added 4-chlorobenzyl mercaptan (95 mg, 0.6 mmol), and the reaction mixture was stirred at room temperature for 2 hours. After the reaction, 3 mL of dichloromethane was added, and the mixture was washed three times with 3 mL of 1N aqueous hydrochloric acid, once with a 0.5 N aqueous sodium hydroxide solution, once with a 4% aqueous sodium bicarbonate solution, and once with saturated brine, and then, the organic layers were dried over magnesium sulfate. Magnesium sulfate was removed by filtration and the solvent was distilled off under reduced pressure, and then 4N hydrochloric acid/ethyl acetate (2 mL) was added and the mixture was allowed to stand at room temperature for 20 minutes. After the reaction, the solvent was distilled off under reduced pressure, and diethyl ether (3 mL) was added and distilled off under reduced pressure. This operation was repeated twice, and then diethyl ether (3 mL) was added and the precipitate was recovered by filtration or centrifugation.

Synthesis of substrates having a DBE is shown below. First, 3,5-dinitrobenzyl chloride (108 mg, 0.5 mmol) and a Boc amino acid (0.6 mmol) and triethylamine (75 mg, 0.75 mmol) were added to dimethylformamide (0.2 mL). After the reaction was continued at room temperature for 12 hours, diethyl ether (8 mL) was added, and the mixture was washed three times with 3 mL of a 1N aqueous hydrochloric acid solution, twice with a 4% aqueous sodium bicarbonate solution, and once with saturated brine, and then the organic layers were dried over magnesium sulfate. Magnesium sulfate was removed by filtration and the solvent was distilled off under reduced pressure, and then 4N hydrochloric acid/ethyl acetate (2 mL) was added and the mixture was allowed to stand at room temperature for 20 minutes. After the reaction, the solvent was distilled off under reduced pressure, and diethyl ether (3 mL) was added and distilled off under reduced pressure. This operation was repeated twice, and then diethyl ether (3 mL) was added and the precipitate was recovered by filtration or centrifugation.

Substrates having a CME were synthesized by a method described (Suga et al., J. Am. Chem. Soc., 120, 1151-1156, 1998) except that deprotection was performed as described above.

Aspartic acid, glutamic acid, cystine, arginine, tryptophan, and glutamine were deprotected as follows. After the esterification reaction, trifluoroacetic acid/dimethyl sulfide=1/1 (2 mL) was added to the residue and the mixture was allowed to stand at room temperature for 30 minutes. After the reaction, the solvent was distilled off under reduced pressure, 2 portions of 4N hydrochloric acid/ethyl acetate (2 mL) were added and the solvent was distilled off under reduced pressure. Further 3 portions of diethyl ether (3 mL) were added and distilled off under reduced pressure. Diethyl ether (3 mL) was added to the residue and the precipitate was recovered by filtration or centrifugation.

The abbreviations for the substrates illustrated in FIG. 6 have the following meanings. Aly: (ε-N-acetyl-L-Lysine), Hbi: (δ-N-biotinyl-(S)-Hydroxybutanoic acid), Cit: (L-Citrulline), Bly: (ε-N-Biotinyl-L-Lysine), Iph: (p-iodo-L-Phenylalanine), Mle: (α-N-methyl-L-Leucine), Bal: (β-Alanine), Dle: (D-Leucine), Hph: ((S)-3-phenyllacetic acid), Hle: (α-Hydroxy-Leucine).

Example 2

This embodiment describes the construction of Superflexizymes and a tRNA molecule (FIG. 7).

In this illustrative embodiment, a synthetic DNA corresponding to the nucleotide sequence of Superflexizyme 1 or 2 (eFxR45 or dnFxR46) was extended with Taq polymerase in the presence of P3 primer (under thermal cycling conditions of 95° C. for 2 min, 50° C. for 1 min, and 72° C. for 10 min), and then amplified with the 5' and 3' primers (P4 and eFxR19 or P4 and dnFxR19) (under thermal cycling conditions of 95° C. for 1 min, 50° C. for 1 min, and 72° C. for 1 min), and the double-stranded DNA was used as a template for in vitro transcription (37° C., for 1 hour) followed by 10% PAGE purification to provide Superflexizymes. Similarly, a tRNA molecule was prepared by amplifying a synthetic DNA corresponding to tRNA$^{Asn}_{CUA}$ (tRNAasncua76) using 5' and 3' primers (tRNAasncua46 and tRNAasncua20) followed by similar steps to provide the intended tRNA.

Superflexizyme 1:

eFxR45:
(SEQ ID NO: 13)
5'-ACCTA ACGCT AATCC CCTTT CGGGG CCGCG GAAAT CTTTC GATCC-3'

P3:
(SEQ ID NO: 14)
5'-GTAAT ACGAC TCACT ATAGG ATCGA AAGAT TTCCG C-3'

P4:
(SEQ ID NO: 15)
5'-GCATA TGTAA TACGA CTCAC TATAG-3' eFxR19:
(SEQ ID NO: 16)
5'-TACCT AACGC TAATC CCCT-3'

Superflexizyme 2:

dnFxR46:
(SEQ ID NO: 17)
5'-ACCTA ACGCC ATGTA CCCTT TCGGG GATGC GGAAA TCTTT CGATC C-3'

P3:
(SEQ ID NOS: 14)
5'-GTAAT ACGAC TCACT ATAGG ATCGA AAGAT TTCCG C-3'

P4:
(SEQ ID NOS: 15)
5'-GCATA TGTAA TACGA CTCAC TATAG-3' dnFxR19:
(SEQ ID NO: 18)
5'-ACCTA ACGCC ATGTA CCCT-3' tRNA$^{Asn}_{CUA}$:
tRNAasncua76:
(SEQ ID NO: 19)
5'-TGGTG CCTCT GACTG GACTC GAACC AGTGA CATAC GGATT TAGAG TCCGC CGTTC TACCG ACTGA ACTAC AGAGG C-3' tRNAasncua46:
(SEQ ID NO: 20)
5'-ACGCA TATGT AATAC GACTC ACTAT AGCCT CTGTA GTTCA GTCGG T-3' tRNAasnuca20:
(SEQ ID NO: 21)
5'-TGGTG CCTCT GACTG GACTC-3'

Example 3

This embodiment shows an example in which the Superflexizymes and tRNA constructed in Example 2 are reacted with the acyl donor substrates synthesized in Example 1.

Although an example of a reaction on a scale of 5 μl is described below, this scale can be changed at will. A solution of the tRNA in 2.5 μl of Reaction Buffer (0.2 M HEPS·K, pH 7.5, 0.2 M KCl) at a concentration of 10-40 μM was heated at 95° C. for 3 minutes and allowed to stand at room temperature for 5 minutes to form the three-dimensional structure of the tRNA. To this was added 1 μl of 3 M MgCl₂ followed by 0.5 μl of an aqueous solution containing 50-200 μM Superflexizyme. To this was added 1 μl of 10-50 mM each acyl donor to initiate the reaction. Under these conditions, the final concentrations of the components are 0.5-20 μM tRNA, 0.5-20 μM Superflexizyme, 2-10 mM acyl donor substrate, 0.1 M Reaction Buffer containing 0.6 M MgCl₂, pH 7.5. This solution was reacted at 0° C. for 1 hour to 24 hours. The reaction was quenched by adding 1.5 volume of 0.6 M NaOAc followed by ethanol precipitation, and the precipitate was washed with 70% ethanol. When the product was to be used for translation or the like, this precipitate was dissolved in water and added to a translation system.

Example 4

Figure 9:
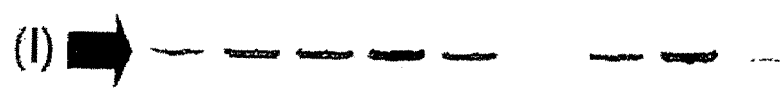
FIG. 9 shows the results of a streptavidin gel shift assay comparing Flexizyme, Superflexizyme 1, and Superflexizyme 2 in the aminoacylation of a tRNA.
Figure 9:
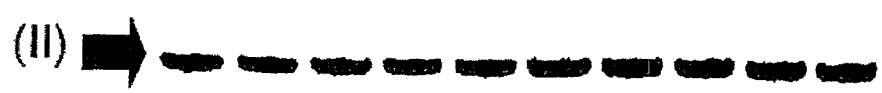
Figure 9:
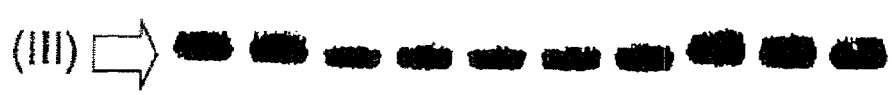

In this embodiment, basic activities of Superflexizymes 1, 2 were evaluated (FIGS. 8-9).

First, Flexizyme and Superflexizyme 2 were compared (FIG. 8). The product aminoacyl-tRNA is typically biotinylated and identified on polyacrylamide gel electrophoresis (PAGE) in the presence of streptavidin. First, the product was dissolved in a solution containing 7 mg/mL sulfosuccinimidyl D-biotin in 0.4 M HEPES K, pH 8.0 (0.01 mL), and reacted at 0° C. for 1 hour to selectively biotinylate RNAs to which an amino acid had been attached. To this was added 1 volume of 0.6 M NaCl followed by ethanol precipitation, and the precipitate was washed three times with 70% ethanol. The recovered product was dissolved in 1.5 µl of Gel Loading Buffer containing streptavidin (0.2 mg/ml streptavidin, 40 mM piperazine, pH 6.1, 40 mM EDTA, 6.4 M urea), and electrophoresed on 12% PAGE, and detected as a slow-migrating band by a streptavidin gel shift assay. Syber Green II (CAMBREX) was used for RNA staining, and FLA-5100 (Fuji) was used for detection.

9), this is a useful feature compensating for drawbacks of Superflexizyme 2.

Example 5

Figure 10:
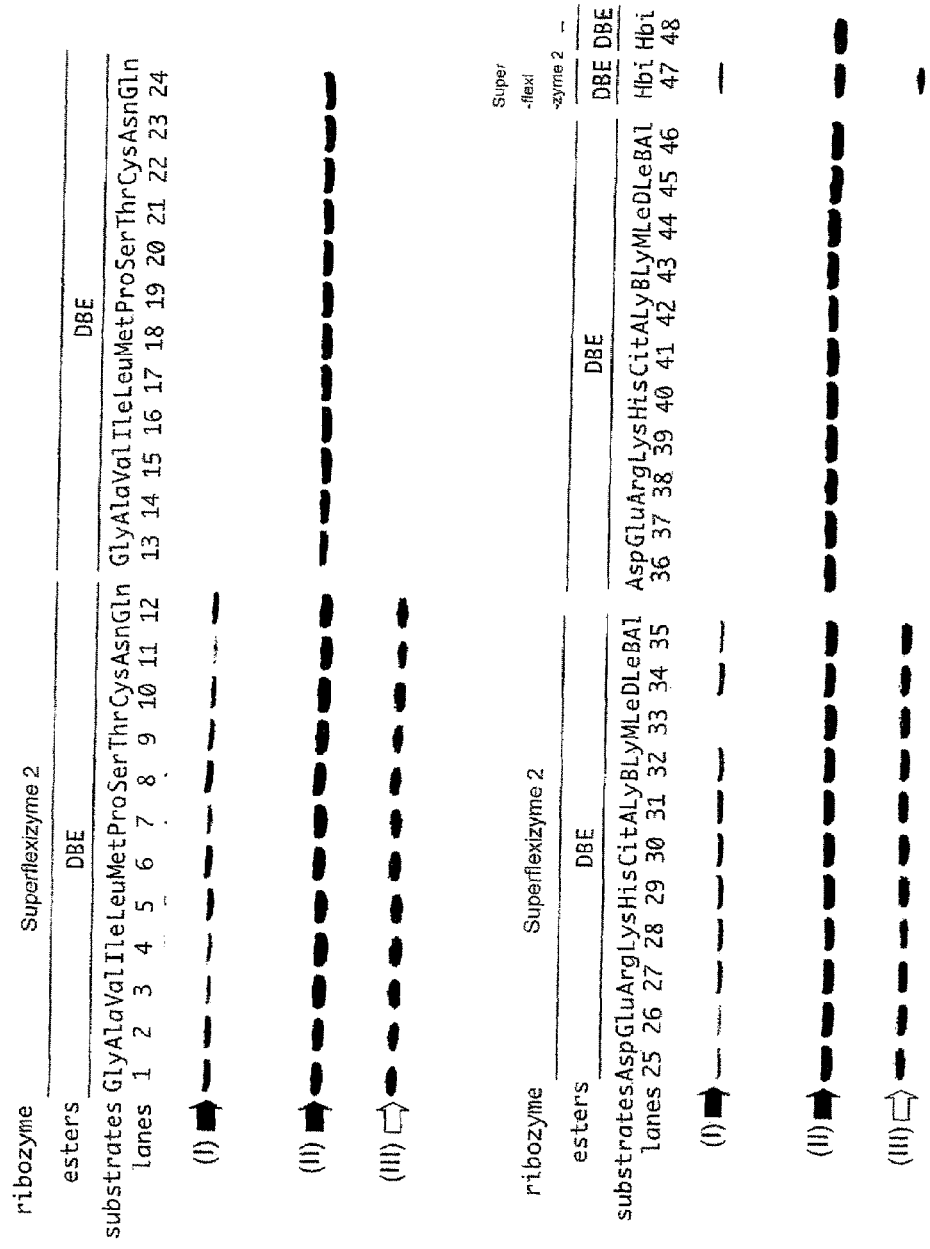
FIG. 10 shows the results of a streptavidin gel shift assay evaluating activities of Superflexizymes 1 and 2 in the acylation of a tRNA or microhelix.
Figure 11:
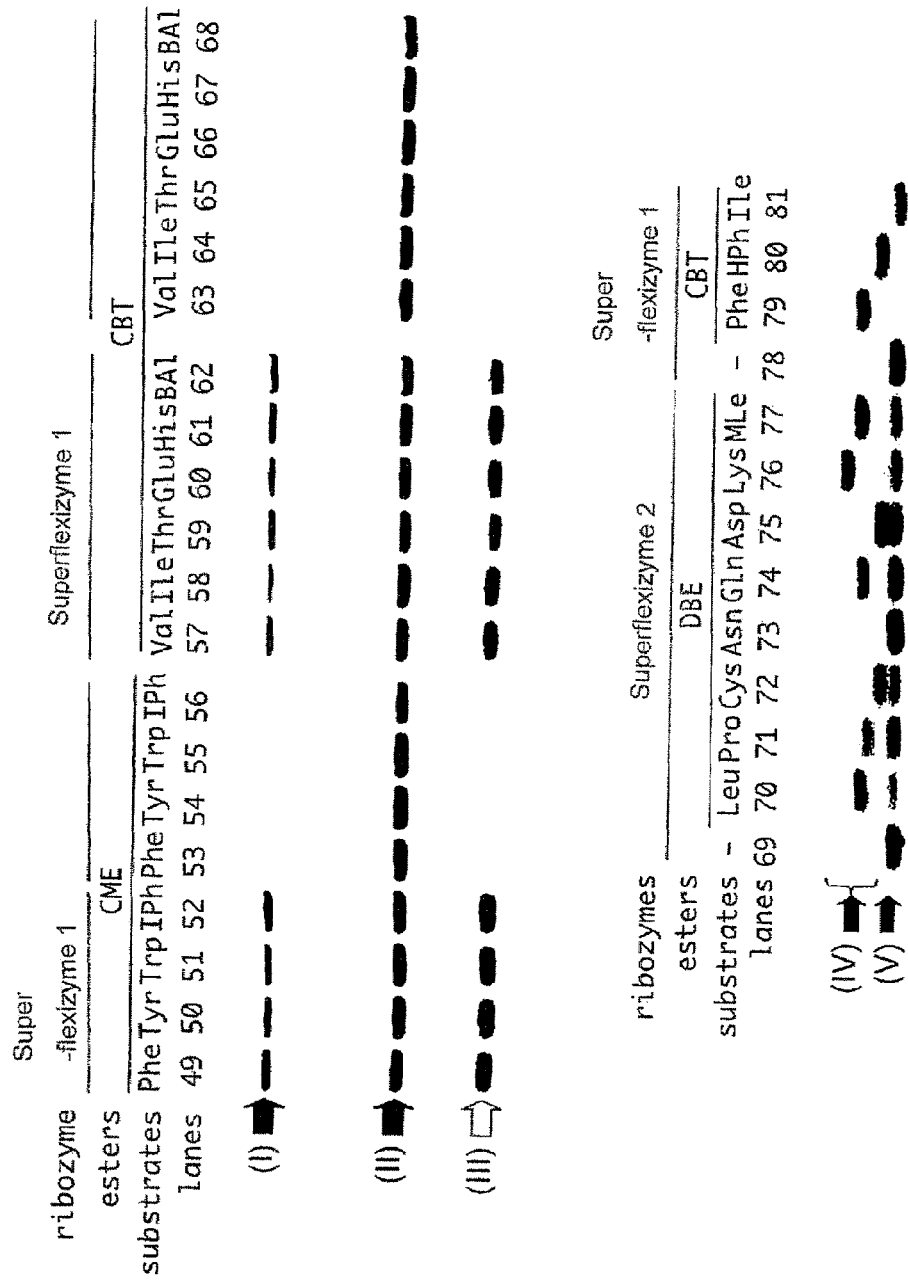
FIG. 11 shows the results of a streptavidin gel shift assay evaluating activities of Superflexizymes 1 and 2 in the acylation of a tRNA or microhelix.

In this embodiment, the activity evaluation of Superflexizymes 1 and 2 shown in Example 4 was performed to assess activity toward the twenty natural amino acids, 9 nonnatural amino acids and lactic acid (FIGS. 10-11, and Table 1 below).

TABLE 1

| Substrates | Time (h) | Yield (%) | S.D. | Substrates | Time (h) | Yield (%) | S.D. |
|---|---|---|---|---|---|---|---|
| Gly-DBE | 2 | 38.9 | 4.5 | Glu-DBE | 2 | 17.5 | 1.8 |
| Ala-DBE | 2 | 35.9 | 3.9 | Glu-CBT | 2 | 31.5 | 4.6 |
| Val-DBE | 6 | 13.1 | 2.8 | Arg-DBE | 4 | 31.2 | 3.3 |
| Val-CBT | 6 | 29.2 | 4.5 | Lys-DBE | 2 | 36.3 | 1.4 |
| Ile-DBE | 6 | 13.6 | 0.9 | Lys-DBE(aPAGE) | 2 | 56.7 | 8.1 |
| Ile-CBT | 6 | 16.7 | 4.9 | His-DBE | 4 | 29.2 | 3.3 |
| Ile-CBT(aPAGE) | 6 | 17.0 | 3.2 | Cit-DBE | 2 | 34.7 | 4.4 |
| Leu-DBE | 2 | 37.3 | 2.2 | Aly-DBE | 2 | 33.4 | 6.6 |
| Leu-DBE(aPAGE) | 2 | 64.2 | 6.4 | Bly-DBE | 4 | 29.9 | 9.5 |
| Met-DBE | 2 | 35.2 | 2.2 | Mle-DBE | 4 | 3.4 | 1.1 |
| Pro-DBE | 2 | 17.2 | 6.9 | Mle-DBE(aPAGE) | 4 | 55.3 | 9.3 |
| Pro-DBE(aPAGE) | 2 | 37.1 | 5.3 | Dle-DBE | 2 | 32.3 | 8.4 |
| Ser-DBE | 4 | 37.5 | 4.9 | Bal-DBE | 6 | 17.3 | 2.9 |
| Thr-DBE | 6 | 24.2 | 4.5 | Bal-CBT | 2 | 39.9 | 1.7 |
| Thr-CBT | 4 | 44.6 | 6.0 | Hbi-DBE | 24 | 25.2 | 1.9 |
| Cys-DBE | 6 | 15.2 | 4.9 | Hle-DBE(aPAGE) | 24 | 51.2 | 1.1 |
| Cys-DBE(aPAGE) | 6 | 46.4 | 6.0 | Phe-CME | 1 | 47.1 | 4.1 |
| Asn-DBE | 2 | 8.0 | 1.9 | Phe-CME(aPAGE) | 1 | 74.5 | 11.9 |
| Asn-DBE(aPAGE) | 2 | 21.5 | 6.3 | Tyr-CME | 1 | 34.4 | 6.4 |
| Gln-DBE | 2 | 24.2 | 4.7 | Trp-CME | 1 | 35.6 | 6.2 |
| Gln-DBE(aPAGE) | 2 | 45.7 | 7.5 | Iph-CME | 1 | 41.5 | 3.4 |
| Asp-DBE | 6 | 18.9 | 2.7 | Hph-CME(aPAGE) | 2 | 81.5 | 5.2 |
| Asp-DBE(aPAGE) | 6 | 52.2 | 1.4 | | | | |

Amino acids having a secondary amino group inefficient for biotinylation, amino acids susceptible to hydrolysis under biotinylation conditions and lactic acid incapable of biotinylation were analyzed using a microhelix RNA in place of the tRNA to directly observe acylation products on acid PAGE. HBi-DBE (δ-N-biotinyl-3-hydroxybutyric acid: δ-N-Biotinyl-(s)-hydroxybutanoic acid) already containing biotin was analyzed by a streptavidin gel shift assay on PAGE without including a biotinylation step.

FIGS. 8-9 show bands for (I) complexes of aminoacyl-tRNA and streptavidin, (II) tRNA, and (III) ribozymes. The aminoacylation yield was calculated from the ratio of band intensities (I)/(II)+(III).

Superflexizyme 2 significantly improved in the activity toward Leu-DBE as compared with Flexizyme (FIG. 8, lanes 3 and 6). However, Superflexizyme 2 decreased in the activity toward Phe-CME (lanes 1 and 4). These results show that Superflexizyme 2 was optimized for substrates having a dinitrobenzyl ester. The activity disappeared when the tRNA oxidized at the 3' end (tRNA-3'(OX)) was used, showing that the acylation proceeded specifically at the 3' end (lanes 7, 10, 12).

Next, Flexizyme and Superflexizymes 1, 2 were compared (FIG. 9). Reaction conditions were as described above. Superflexizyme 1 improved in the activity toward Phe-CME as compared with Flexizyme (lanes 1, 3). Superflexizyme 1 improved in the activity toward substrates having a dinitrobenzyl ester, but the activity was lower than that of Superflexizyme 2 (lanes 5 and 8). However, substrates having a thioester bond were found to be compatible with Superflexizyme 1, but not with Superflexizyme 2 (lanes 7, 10). Considering the modest activity toward substrates consisting of β-branched amino acids having a dinitrobenzyl ester (lanes 6, Table 1 Yield of Aminoacyl-tRNA (Time: Reaction Time)

Reaction conditions were as described in Example 3 except that the substrate concentration was increased from 1 mM to 5 or 10 mM because the reaction efficiency is assumed to vary among amino acids. For the reaction time, see Table 1 (Time) Cystine was used for the reaction after it had been converted into cysteine by reducing the disulfide bond with DTT. Lanes 1-56 show denaturing PAGE, while lanes 57-69 show denaturing acid PAGE (acid PAGE). Denaturing PAGE was performed in the same manner as in Example 4, and denaturing acid PAGE was performed by using a microhelix (an RNA having a structure further simplified from an altered amber suppressor tRNA$^{Asn}$ derived from E. coli) in place of the tRNA to detect bands of products shifted by molecular mass changes and positive charge increases due to acylation.

FIGS. 10-11 show bands for (I) complexes of aminoacyl-tRNA and streptavidin, (II) tRNA, (III) ribozymes, (IV) aminoacyl-microhelix, and (V) microhelix.

First, the activity of Superflexizyme 2 toward dinitrobenzyl esters of amino acids lacking an aromatic group in the side chain (shown by amino acid abbreviations-DBE in the column of Substrates in Table 1) was evaluated. It is shown that in the presence of Superflexizyme 2, acylated tRNAs could be synthesized in the all amino acids (lanes 1-12, 25-35, 47). In the absence of the Superflexizyme, the tRNA was not acylated at all (lanes 13-24, 36-46, 48), showing that this reaction was catalyzed by Superflexizyme 2. However, the aminoacylation yield varies. Among others, Mle cannot be biotinylated during specific biotinylation because of the low nucleophilicity of the α-amino group. The aminoacylation yield apparently decreased in Asp probably because the carbonyl group in the side chain promotes hydrolysis. To verify this, acid PAGE (aPAGE) was performed by using a microhelix in place of the tRNA. Microhelices are very smaller than tRNAs so that they are relatively significantly influenced by molecular mass changes and charge changes due to aminoacylation. The results showed that acylation proceeded to 50% or more with both Mle and Asp, verifying that the aminoacylation was efficient (lanes 75, 77, aPAGE in Table 1). The mobilities of other amino acids varied with the sizes and charges of substrates, showing that the microhelix was acylated with each substrate. Moreover, the acylation yield is about 1.5- to 1.8-fold higher than that of the tRNA. This is probably because extra nucleotides are less often added to microhelices than to tRNAs by T7 RNA polymerase during RNA transcription. In fact, it was found that extra nucleotides are had been added to the 3' end in about 40% of the tRNA. Thioesters (CBT) of β-branched amino acids (Val, Ile, Thr) and Glu, His and Bal associated with relatively low yields were also tested in the reaction using Superflexizyme 1. Yield improvements were observed in the all amino acids (lanes 57-62, lanes 81, shown by amino acid abbreviation-CBT in Table 1). The reaction did not proceed in the absence of the ribozyme, showing that these reactions were catalyzed by Superflexizyme 1. Substrates having an aromatic group in the side chain were also reacted. Our previous study reported Phe derivatives having a substituent at the p-position (lanes 49, 50, 52, shown by amino acid abbreviations-CME), but a more recent study revealed that amino acids having an aromatic group in the side chain such as Trp (lane 51) serve as substrates. Phenyllactic acid having a hydroxyl group in place of an α-amino group (HPh: (s)-3-phenyllacetic acid) was also found to serve as a substrate (lane 80), showing the applicability of the ribozyme to a wide range of substrates.

Example 6

Figure 12:
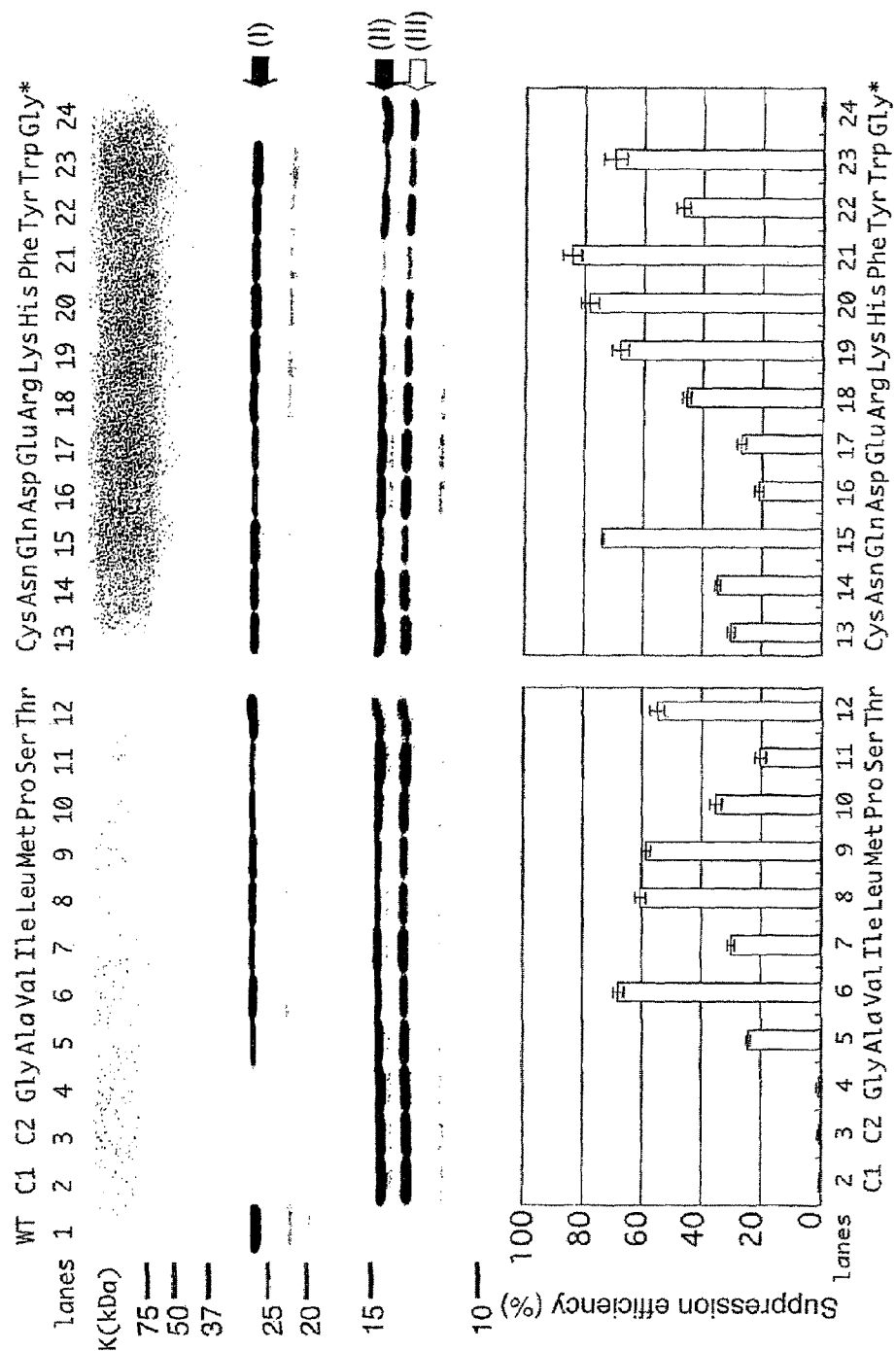
FIG. 12 shows site-specific incorporation of various carboxylic acid substrates into GFP. The upper panels show the results of SDS-PAGE of translation reaction products, and the lower graphs show suppression efficiencies.
Figure 13:
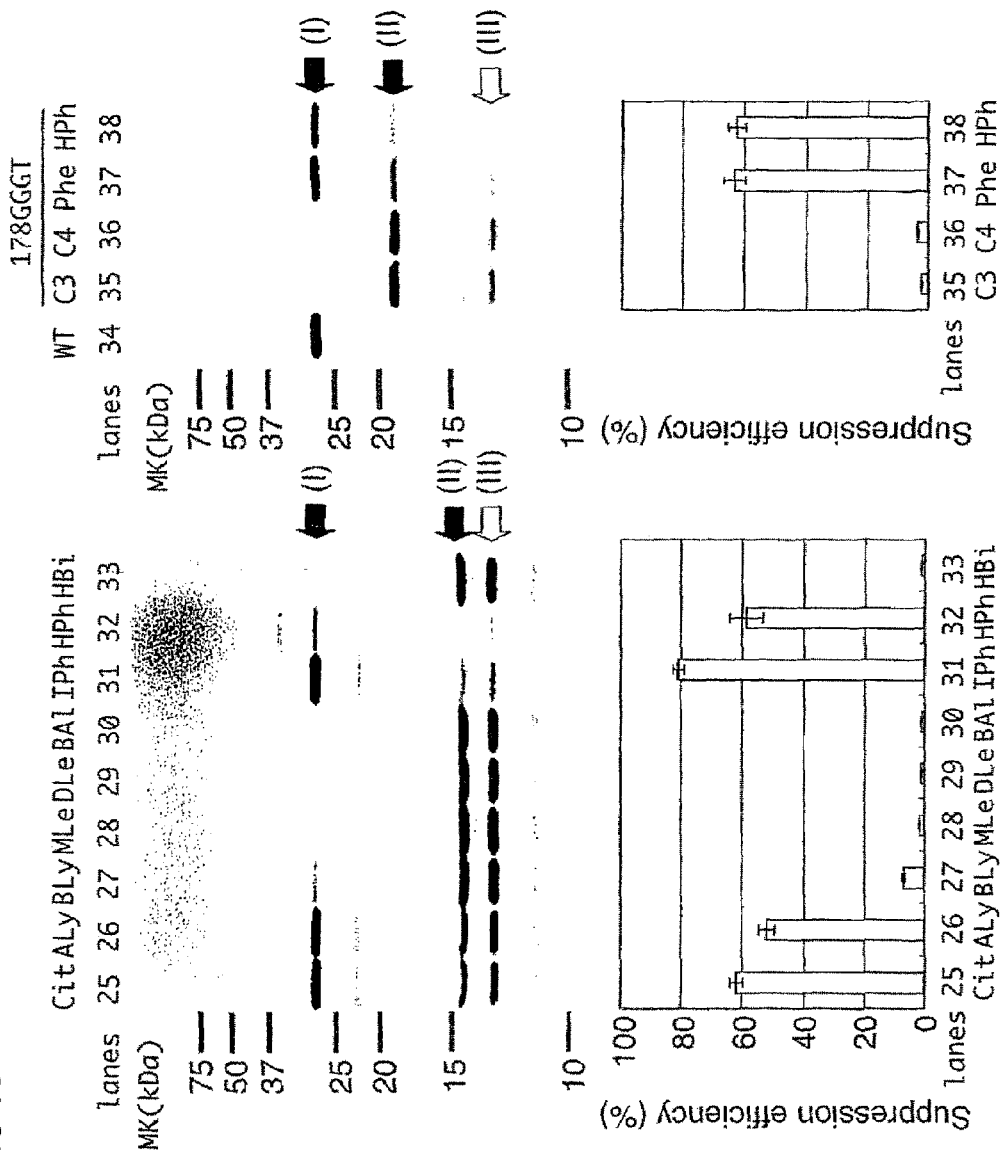
FIG. 13 shows site-specific incorporation of various carboxylic acid substrates into GFP. The upper panels show the results of SDS-PAGE of translation reaction products, and the lower graphs show suppression efficiencies.

In this embodiment, the suppressor aminoacyl-tRNAs prepared in Examples 3-5 were added to a high-efficiency in vitro protein synthesis system RTS-100 from Roche to synthesize proteins (FIGS. 12-13).

Experimental procedures are essentially as described in our previous study that used GFP (Green Fluorescent Protein) as a model protein (Murakami, H., Kourouklis, D. and Suga, H. (2003). "Using a solid-phase ribozyme aminoacylation system to reprogram the genetic code." Chem. Biol. 10(11): 1077-84). GFP can be used to conveniently detect protein synthesis by fluorescence.

Proteins synthesized in the presence of $^{35}$S-labeled Met were analyzed by SDS-PAGE. The suppression efficiency (%) was calculated by the equation below:

Suppression efficiency=$(I)/[(I)+(II)\times3/5]$ where the intensities of the band for the full-length protein (I) and the band for a truncated protein (II) were corrected to reflect the number of Met residues contained therein, and (III) represents a band for an unidentified truncated protein.

FIGS. 12-13 show the results of reactions of WT: wild-type, C1 (lane 2): no tRNA$^{Asn}_{CUA}$, and C2 (lane 3): tRNA$^{Asn}_{CUA}$ alone. Lanes 4-24 represent reactions of aminoacylated tRNA$^{Asn}_{CUA}$ charged with natural amino acids, and lanes 25-33 represent reactions of acylated tRNA$^{Asn}_{CUA}$ charged with modified amino acids, nonnatural amino acids, or lactic acid. The figures also show the results of reactions of C3 (lane 35): no tRNA$^{Asn}_{ACCC}$, and C4 (lane 36): tRNA$^{Asn}_{ACCC}$ alone. Lanes 37-38 represent reactions of acylated tRNA$^{Asn}_{ACCC}$ charged with phenylalanine (Phe) or phenyllacetic acid (HPh).

First, an mRNA is synthesized by T7 RNA polymerase in a reaction system by adding the gene for GFP in which the Tyr codon at position 151 (UAC) has been replaced by a stop codon (TAG). If no tRNA is added, the full-length protein is not synthesized because the TAG codon acts as a stop codon to terminate translation at position 151 (FIG. 12, lane 2). The full-length protein is not synthesized again when an unacylated tRNA is added (lane 3), showing that the suppressor tRNA used cannot serve as a substrate for the ARS in the system. In contrast, a band for the full-length GFP appeared when a suppressor tRNA aminoacylated with Leu was added, showing that a protein having Leu specifically incorporated at position 151 could be synthesized (lanes 1, 8). Similar incorporations of other natural amino acids were observed, with the suppression efficiencies correlating with the aminoacylation yields. However, the incorporation of Gly could not be observed in this study, though the aminoacylation with it was observed (lane 4). Thus, a tRNA aminoacylated with Gly was prepared using Superflexizyme 1 in place of Superflexizyme 2 and added to the system, but its incorporation could not be observed (lane 24). This may result from problems with the translation system but not the ribozyme because the aminoacylation can be observed specifically at the 3' end as apparent from the fact that the tRNA oxidized at the 3' end was not aminoacylated. This point is now under investigation, and we wish to clarify the reason in future.

Incorporation of nonnatural amino acids was also attempted. The incorporation of IPh had been directly observed by analyzing the same sample by a mass spectrometer in our previous study (FIG. 13, lane 31). Cit and Aly were efficiently incorporated (lanes 25, 26). In contrast, the incorporation efficiency of an amino acid having biotin in the side chain was low (lane 27). This low suppression efficiency may be attributed to the fact that biotin was too large to be efficiently accepted by the ribosome because the aminoacylation yield was about 30% comparably to Cit and ALy. Incorporation of MLe, DLe, BAl was also attempted, but the incorporation efficiencies were below detection limits (lanes 28-30). The 3'-specific aminoacylation could be demonstrated by the fact that an oxidized form of the tRNA was not aminoacylated. Our previous study reported incorporation of α-methylamino acids, D-amino acids, and β-amino acids, but these amino acids were found not to be efficiently incorporated into the ribosome at least in the system used in this example. Incorporation of lactic acid (HBi) was also attempted. Incorporation of lactic acid having biotin in the side chain could not be observed for the same reason as described above (lane 33). In contrast, incorporation of phenyllacetic acid (Hph) was observed with high efficiency (lane 32). However, a band appeared above the position corresponding to the mobility of the full-length protein. This may result from a transfer caused by a nucleophilic attack on the ester bond by another side chain. Thus, phenyllacetic acid (Hph) was introduced into position 178 of the gene having a four-base codon (GGGT) at position 178 prepared in our previous study. At this position, only the full-length protein was produced (lane 38). This means that the slow mobility band described above was produced specifically at position 151 for some steric reason. Anyway, lactic acid was also a substrate efficiently incorporated into the ribosome in this translation system.

The invention claimed is:

1. A ribozyme catalyzing tRNA acylation having a structure consisting of an RNA sequence represented by the general formula below:

P1-CCGC($N^1$)$_1$($N^1$)$_2$...($N^1$)$_p$-P2-($N^2$)$_1$($N^2$)$_2$...($N^2$)$_q$GCG($N^3$)$_1$($N^3$)$_2$AGG$\underline{N}$ wherein P1 and P2 represent a domain consisting of any RNA sequence capable of having a stem-loop structure; ($N^1$)$_1$-($N^1$)$_p$ each independently represent any monoribonucleotide of U, C, A or G; p represents 3 or 4; ($N^2$)$_1$-($N^2$)$_q$ each independently represent any monoribonucleotide of U, C, A or G; q represents 5 or 6; ($N^3$)$_1$-($N^3$)$_2$ each independently represent any monoribonucleotide of U, C, A or G; U represents an uracil nucleotide; C represents a cytosine nucleotide; A represents an adenine nucleotide; G represents a guanine nucleotide; and $\underline{N}$ represents a monoribonucleotide complementary to $\overline{A}$ or G;

wherein the ribozyme recognizes a tRNA via the 3'-terminal GG$\underline{N}$ motif to bind the tRNA and said GG$\underline{N}$ motif is complementary to a nucleotide sequence at positions 75-73 at the 3' end of the tRNA binding the ribozyme, and wherein the structure of the ribozyme catalyzing tRNA acylation consists of an RNA sequence represented by formula (I) or (II) below:

P1-CCGCGGC-P2-GAUUAGCGUUAGG$\underline{N}$ (I)  (SEQ ID NOS: 1 and 2)

P1-CCGCAUC-P2-UACAUGGCGUUAGG$\underline{N}$ (II). (SEQ ID NOS: 3 and 4)

2. The ribozyme of claim 1 wherein P1 and P2 each independently consist of an RNA sequence represented by the formula below:

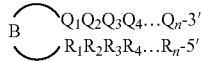

wherein B represents any single-stranded loop consisting of 1-8 ribonucleotides selected from U, C, A and G; Q1-Qn each independently represent any monoribonucleotide of U, C, A or G; R1-Rn represent any monoribonucleotide of U, C, A or G selected in such a manner that they can preferentially assume a double-stranded structure by forming wholly or partially complementary base pairs with Q1-Qn; and n represents an integer of 1-10.

3. The ribozyme of claim 2 wherein the single-stranded loop represented by B is a stable tetraloop.

4. The ribozyme of claim 1 wherein P1 and P2 consist of RNA sequences represented by:

P1: GGAUCGAAAGAUUU;  (SEQ ID NO: 5)

P2: CCCGAAAGGG.  (SEQ ID NO: 6)

5. A ribozyme catalyzing tRNA acylation according to claim 1 wherein the structure consists of any one of RNA sequences (a)-(d) below:

(a)                                            (SEQ ID NO: 7)
GGAUCGAAAGAUUUCCGCGGCCCCGAAAGGGAUUAGCGUUAGGU;

(b)                                            (SEQ ID NO: 8)
GGAUCGAAAGAUUUCCGCAUCCCCGAAAGGGUACAUGGCGUUAGGU;

(c) an RNA sequence identical to sequence (a) except that U at the 3' end has been replaced by any nucleotide designed to be complementary to nucleotide 73 in the tRNA to be acylated; and (d) an RNA sequence identical to sequence (b) except that U at the 3' end has been replaced by any nucleotide designed to be complementary to nucleotide 73 in the tRNA to be acylated.

6. The ribozyme of claim 1, which catalyzes tRNA acylation with a natural amino acid, a nonnatural amino acid, or lactic acid.

7. A polynucleotide comprising any one of (a)-(d) below in the molecule:

(a) an RNA constituting the ribozyme of claim 1;
(b) an RNA consisting of a sequence complementary to the RNA of (a) above;
(c) a DNA consisting of a sequence identical to the RNA of (a) above, but U is replaced by T; and
(d) a DNA consisting of a sequence identical to the RNA of (b) above, but U is replaced by T.

8. A process for preparing an acylated tRNA, comprising the steps of:

(a) providing one or more ribozymes of claim 1;
(b) providing a tRNA;
(c) providing a modestly activated carboxylic acid;
(d) contacting the ribozyme with the tRNA and the modestly activated carboxylic acid to acylate the tRNA; and
(e) isolating the acylated tRNA.

9. The process of claim 8 wherein the carboxylic acid is a natural amino acid, nonnatural amino acid, or lactic acid.

10. The process of claim 8 wherein the modestly activated carboxylic acid is an esterified derivative of an amino acids, a thioesterified derivative of an amino acid, or an esterified derivative of a carboxylic acid.

11. The process of claim 8 wherein the modestly activated carboxylic acid is selected from:
   cyanomethyl esters of natural amino acids or nonnatural amino acids having an aromatic ring in the side chain;
   3,5-dinitrobenzyl esters of natural amino acids or nonnatural amino acids;
   4-chlorobenzyl thioesters of natural amino acids or non-natural amino acids;
   cyanomethyl esters of phenyllacetic acid; and
   3,5-dinitrobenzyl esters of phenyllacetic acid or alkyllactic acid.

12. The process of any one of claims 8 to 11 wherein the ribozyme is immobilized to a support.

13. A process for preparing an acylated tRNA according to claim 10, comprising the steps of:
   (a) providing two ribozymes catalyzing tRNA acylation, each consisting of an RNA sequence of (1) or (2) below:

```
                                             (SEQ ID NO: 7)
(1) GGAUCGAAAGAUUUCCGCGGCCCCGAAAGGGGAUUAGCGUUAGGU (SEQ ID NO: 8)
(2) GGAUCGAAAGAUUUCCGCAUCCCCGAAAGGGUACAUGGCGUUAGGU
```

(b) providing a tRNA;
   (c) providing an esterified derivative or thioesterified derivative of a natural amino acid, nonnatural amino acid or lactic acid;
   (d) contacting the ribozymes with the tRNA and the esterified derivative or thioesterified derivative of a natural amino acid, nonnatural amino acid or lactic acid to acylate the tRNA; and
   (e) isolating the acylated tRNA.

14. A kit capable of being used to obtain a tRNA molecule acylated with a natural amino acid, nonnatural amino acid, or lactic acid, comprising:
   (a) one or more ribozymes of claim 1;
   (b) an esterified derivative or thioesterified derivative of a natural amino acid, nonnatural amino acid, or lactic acid used as a substrate for the ribozymes; and
   (c) a tRNA.

15. A process for preparing a polypeptide containing any nonnatural amino acid or other carboxylic acid incorporated at a desired site, comprising steps:
   (a) providing one or more ribozymes of claim 1;
   (b) acylating a tRNA with a nonnatural amino acid or carboxylic acid using the ribozyme;
   (c) providing an mRNA having a codon complementary to the anticodon of the tRNA at a desired site; and
   (d) adding the acylated tRNA and the mRNA to a translation system to prepare a polypeptide containing the nonnatural amino acid or carboxylic acid incorporated at the desired site.

16. The process of claim 15 wherein the carboxylic acid is lactic acid.

17. The process of claim 15 or 16 wherein the tRNA has an anticodon corresponding to a stop codon, a four-base anticodon, an anticodon containing an artificial nucleotide, or an anticodon complementary to a codon encoding a natural amino acid.

18. The process of claim 15, further comprising the step of separating the acylated tRNA from the ribozyme before it is added to a translation system in step (d).

\* \* \* \* \*